US010350027B2

(12) United States Patent
Ritter

(10) Patent No.: US 10,350,027 B2
(45) Date of Patent: Jul. 16, 2019

(54) ILLUMINATED DENTAL INSTRUMENT ASSEMBLIES AND COMPONENTS FOR USE WITHIN ILLUMINATED DENTAL INSTRUMENT ASSEMBLIES

(71) Applicant: Austin R. Ritter, Spring Lake, MI (US)

(72) Inventor: Austin R. Ritter, Spring Lake, MI (US)

(*) Notice: Subject to any disclaimer, the term of this patent is extended or adjusted under 35 U.S.C. 154(b) by 0 days.

(21) Appl. No.: 15/807,465

(22) Filed: Nov. 8, 2017

(65) Prior Publication Data

US 2018/0132970 A1 May 17, 2018

Related U.S. Application Data

(60) Provisional application No. 62/422,669, filed on Nov. 16, 2016, provisional application No. 62/422,927, filed on Nov. 16, 2016, provisional application No. 62/423,607, filed on Nov. 17, 2016.

(51) Int. Cl.

| A61B 1/07 | (2006.01) |
|---|---|
| A61C 1/08 | (2006.01) |
| A61B 1/00 | (2006.01) |
| A61B 13/00 | (2006.01) |
| A61C 5/88 | (2017.01) |
| A61C 5/90 | (2017.01) |
| A61B 1/247 | (2006.01) |
| A61C 5/80 | (2017.01) |

(52) U.S. Cl.
CPC .......... *A61C 1/088* (2013.01); *A61B 1/00126* (2013.01); *A61B 1/07* (2013.01); *A61B 1/247* (2013.01); *A61B 13/00* (2013.01); *A61C 5/88* (2017.02); *A61C 5/90* (2017.02); *A61C 5/80* (2017.02)

(58) Field of Classification Search
CPC .............................. A61B 1/247; G02B 6/3604
See application file for complete search history.

(56) References Cited

U.S. PATENT DOCUMENTS

| 3,382,408 A * | 5/1968 | Atkins | A61B 1/247 |
| | | | 307/652 |
| 3,614,415 A * | 10/1971 | Edelman | A61B 1/247 |
| | | | 362/119 |
| 3,638,013 A * | 1/1972 | Keller | A61B 1/07 |
| | | | 362/120 |
| 4,641,915 A * | 2/1987 | Asakawa | G02B 6/3886 |
| | | | 385/26 |

(Continued)

*Primary Examiner* — Ralph A Lewis
(74) *Attorney, Agent, or Firm* — James E. Shultz, Jr.

(57) ABSTRACT

Illuminated dental instrument assemblies (e.g., illuminated dental mirrors, illuminated dental wedges, trans-illumination dental instrument, illuminated dental bite blocks, etc.) are provided. The illuminated dental instrument assemblies may be adapted to be periodically sterilized. The illuminated dental instrument assemblies may include a magnetically energetic fiber optic coupler. The magnetically energetic fiber optic coupler may be configured to allow the illuminated dental instrument assembly to rotate with respect to an associated fiber optic cable that is removably connected to the magnetically energetic fiber optic coupler. The illuminated dental instrument assemblies may include a fiber optic material that is encapsulated.

20 Claims, 28 Drawing Sheets

(56) References Cited

U.S. PATENT DOCUMENTS

| | | | | |
|---|---|---|---|---|
| 4,690,495 | A * | 9/1987 | Giannini | G02B 6/32 |
| | | | | 385/57 |
| 5,960,140 | A * | 9/1999 | Caplan | A61B 1/07 |
| | | | | 385/87 |
| 8,172,571 | B2 * | 5/2012 | Watson | A61B 1/253 |
| | | | | 433/31 |
| 9,360,630 | B2 * | 6/2016 | Jenner | G02B 6/3604 |
| 9,869,826 | B1 * | 1/2018 | Shang | G02B 6/3886 |
| 10,088,638 | B2 * | 10/2018 | Yajima | G02B 23/26 |
| 2002/0117849 | A1 * | 8/2002 | Bailey | A61C 1/18 |
| | | | | 285/123.15 |

\* cited by examiner

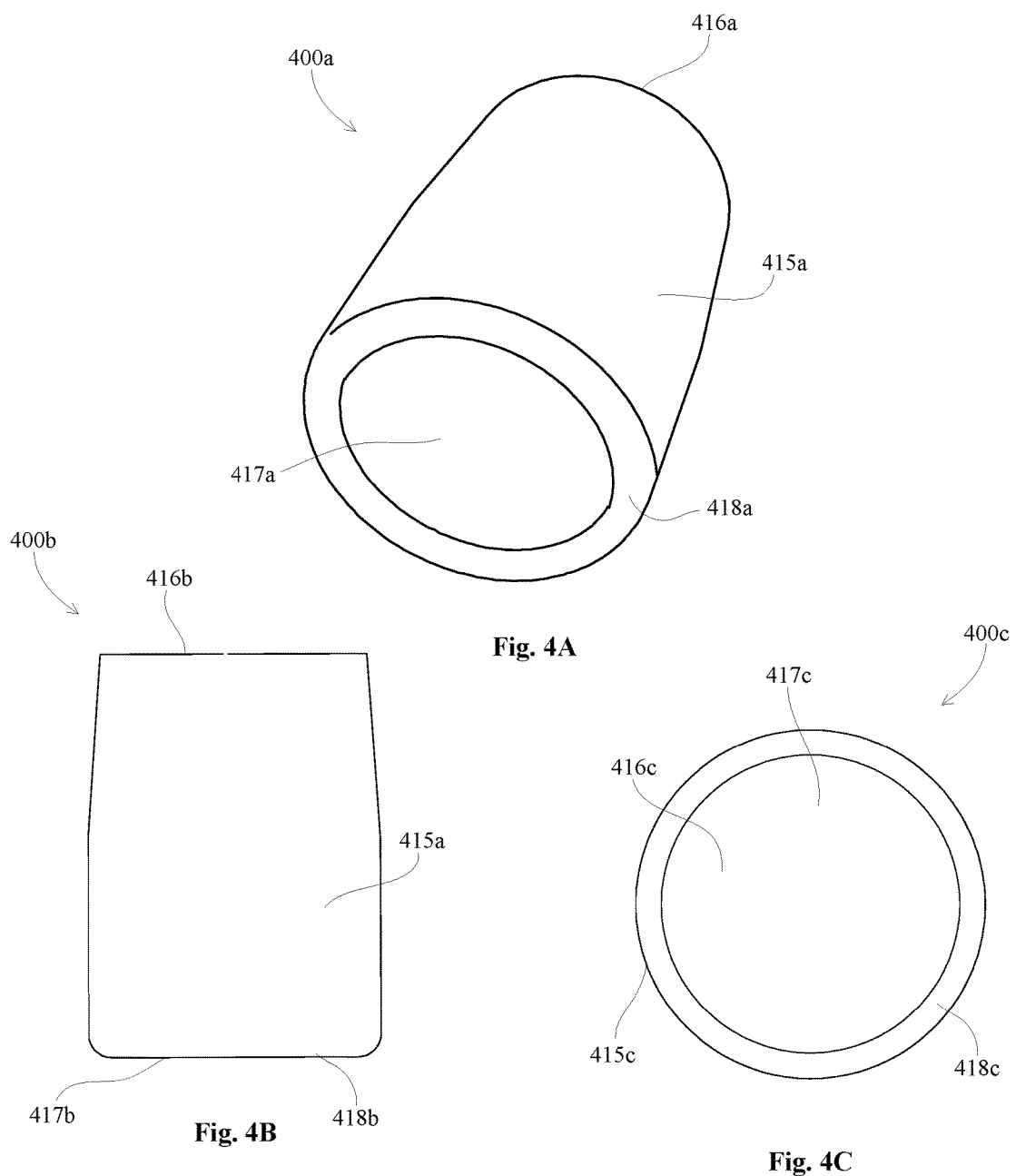

ILLUMINATED DENTAL INSTRUMENT ASSEMBLIES AND COMPONENTS FOR USE WITHIN ILLUMINATED DENTAL INSTRUMENT ASSEMBLIES

CROSS-REFERENCE TO RELATED APPLICATIONS AND CLAIM TO PRIORITY

The present application claims priority under 35 U.S.C. § 119(e) of U.S. Provisional Application Ser. No. 62/422,669, entitled Magnetically Coupled Fiber Optic Lighted Dental Mirror, filed Nov. 16, 2016; 62/422,927, entitled Magnetically Coupled Fiber Optic Tooth Illumination Pick Light Tool for Dentistry, filed Nov. 16, 2016; and 62/423,607, entitled Illuminated Dental Wedge, filed Nov. 17, 2016; the entire disclosures of which is incorporated herein by reference.

TECHNICAL FIELD

The present disclosure generally relates to illuminated dental instrument assemblies (e.g., illuminated dental mirrors, illuminated dental wedges, illuminated dental picks, illuminated dental bite blocks, etc.) and components for use within illuminated dental mirror assemblies. More particularly, the present disclosure relates to illuminated dental instrument assemblies that are adapted to be periodically sterilized.

BACKGROUND

Dental procedures and/or examinations often require a dentist and/or dental hygienist to work under numerous limitations, primarily among them being restricted physical access available for performing dental procedures within a patient's mouth and limited ambient light. For example, during dental procedures, the patient's mouth must often times receive a dental hand instrument, a dental drill unit, a saliva ejection tube to evacuate particulates and/or saliva from the patient's mouth during the dental procedure, which typically require assistance of a another person, such as a dental assistant. In addition, use of dental accessories (e.g., light sources, tongue depressors, dental mirrors, etc.) is occasionally required.

Use of optoelectronic devices having external light sources (e.g., an overhead light source, a dentist head-mounted light source, etc.) require alignment of the external light source and/or the patient's head to be periodically adjusted during a dental procedure. Periodic realignment of either the patient's head or an external light source often requires the dentist to be distracted and, is at best, cumbersome. Frequently, dental instuments, used during dental procedures, often block or create shadows that prohibit external light from reaching an associated mirror and/or a work area needing light to aid in the procedure being performed.

Prior attempts to introduce a light source, that emit light or provide luminous emittance from inside the patient's mouth, add further obstruction and/or limit access for performance of dental procedures and typically required use of two hands, or a dental assistant, to attach or remove the light source. Known illuminated dental mirrors include light sources that generate unacceptable heat. Moreover, prior attempts to introduce an inter-oral light source, from which the light is emitted, from within a patient's mouth have not accounted for the need to periodically sterilize the light source after every use.

Prior attempts to introduce illuminated dental instruments inside a patient's mouth included associated instruments having rough surfaces and/or couplers with crevices to which bacteria and blood attached. Prior attempts also failed to project high enough LUX with an acceptable color temperature (Kelvin) to aid in trans-illumination of teeth for assistance in diagnoses. Furthermore, attempts to use a lighted dental mirror for long periods of time or hours of continuous use in a dental practice each and every day have been cost prohibitive and unreliable. Hence, an illuminated dental instrument (e.g., an illuminated dental mirror, an illuminated dental wedge, an illuminated dental bite block, an illuminated dental pick, etc.) assembly which overcomes these drawbacks would be advantageous.

SUMMARY OF THE INVENTION

An illuminated dental instrument assembly may include a fiber optic cable coupler including a magnetically energetic material. The fiber optic cable coupler may be configured to allow the illuminated dental instrument assembly to rotate with respect to an associated fiber optic cable. The illuminated dental mirror may also include a handle that at least partially encapsulates a fiber optic element within a handle material that does not degrade when sterilized in an autoclave. An illuminated dental instrument assembly may include smooth surfaces and light couplers free of crevices, such that bacteria and blood may not attach to the illuminated dental instrument assembly.

An illuminated dental instrument assembly may include an axially magnetized linear fiber optic coupling system. An axially magnetized linear fiber optic coupler may reduce binding and allow quick and easy engagement (e.g., may only require one hand of a user). An axially magnetized linear fiber optic coupler may reduce, or eliminate, associated wear. An illuminated dental instrument assembly may project high enough LUX with an acceptable color temperature (Kelvin) to aid in trans-illumination of teeth for assistance in diagnoses.

In another embodiment, an illuminated dental instrument assembly may include a fiber optic cable coupler. The fiber optic cable coupler may be configured to allow the illuminated dental instrument assembly to rotate with respect to an associated fiber optic cable. The illuminated dental mirror may also include a handle that at least partially encapsulates a fiber optic element within a handle material that does not degrade when sterilized in an autoclave.

In a further embodiment, an illuminated dental instrument assembly may include a fiber optic cable coupler including a magnetically energetic material. The fiber optic cable coupler may be configured to allow the illuminated dental instrument assembly to rotate with respect to an associated fiber optic cable. The illuminated dental mirror may also include a handle having a fiber optic element extending from a proximal end of the handle to a distal end of the handle.

These and other aspects, objects, and features of the present invention will be understood and appreciated by those skilled in the art upon studying the following specification, claims, and appended drawings.

BRIEF DESCRIPTION OF THE DRAWINGS

FIGS. 4A-4C depict various views of an example end cap/coupling lens for use within the illuminated dental mirror assembly of FIGS. 2A-2C;

DETAILED DESCRIPTION

Figure 1:
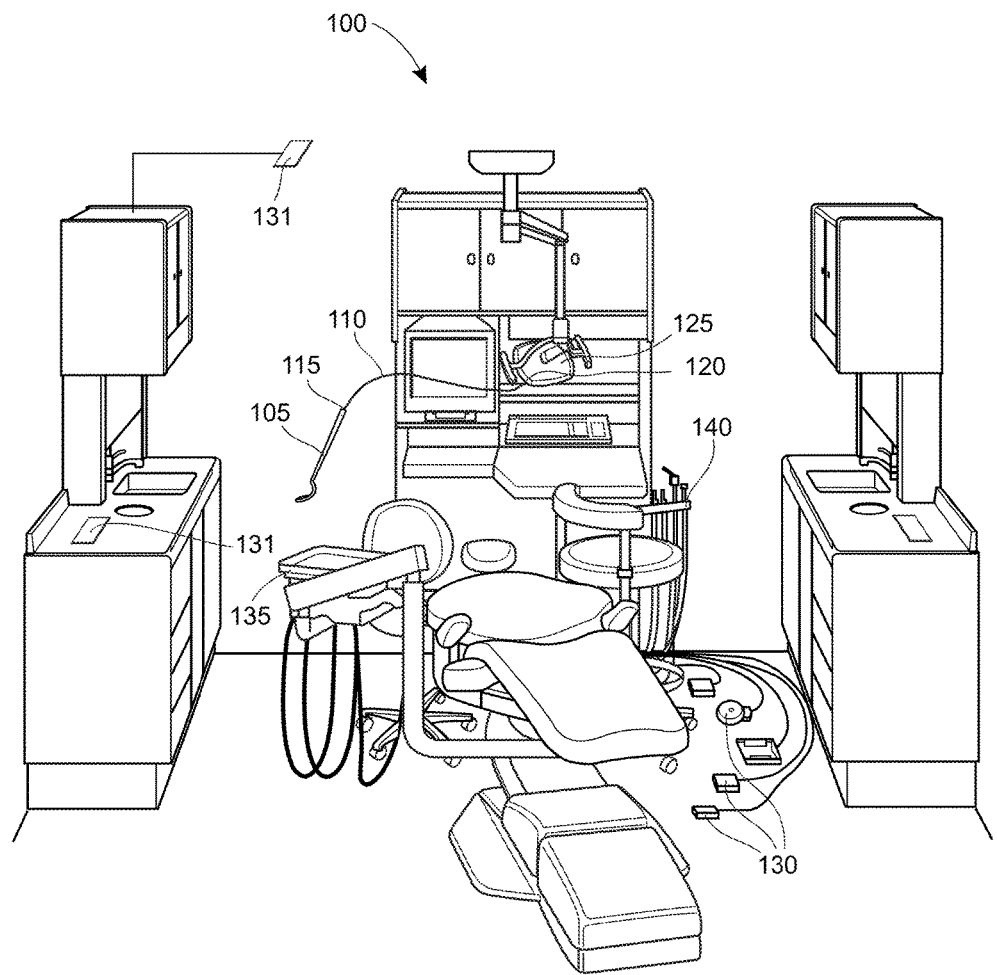
FIG. 1 depicts an illuminated dental mirror assembly in use within a dental operatory room.

Illuminated dental mirror assemblies and components for use within illuminated dental mirror assemblies are provided. The illuminated dental mirror assemblies may be sterilized in, for example, an autoclave or a chemical solution after use with a given patient. The illuminated dental mirror assembly components may include materials that withstand exposure to high temperatures. Exterior components of the illuminated dental mirror assemblies may include materials that withstand exposure to high temperatures and chemicals used for sterilization.

An illumination source may be communicatively connected to an illuminated dental mirror assembly via, for example, a fiber optic cable via at least one rotatable fiber optic coupler. The rotatable fiber optic coupler may be a magnetic light coupler (e.g., a magnetic light coupler as disclosed in commonly assigned U.S. Patent Application Publication No. 20160310234). The fiber optic cable may include a magnetic light coupler on each end (i.e., a first magnetic light coupler may connect to the light source and a second magnetic light coupler may connect to the illuminated dental mirror assembly).

As described in detail herein, an illuminated dental mirror may include a fiber optic element, within an interior of an associated handle, and extending between a magnetic light coupler on a first end of the handle to an optic element on a second end of the handle proximate an accompanying mirror. The fiber optic element may be encapsulated within other materials that may provide rigidity and/or isolation from an environment surrounding the illuminated dental mirror assembly (e.g. a dentist's hands, a dental assistant's hands, an interior of a dental patient's mouth, chemical sterilization, an autoclave, etc.). A fiber optic element may convey, and an illuminated dental mirror assembly may emit, for example, 80,000 LUX toward the mirror.

As referenced in the figures, the same reference numerals may be used herein to refer to the same parameters and components or their similar modifications and alternatives. For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

Turning to FIG. 1, a dental operatory room 100 may include an illuminated dental mirror 105 interconnected with a light source 125 (e.g., a reorientable overhead light source) via a fiber optic cable 110, a first magnetic light coupler 115 and a second magnetic light coupler 120. The light source 125 may include, for example, a light engine (e.g., Model No. HYLUX-STM-B, as available from Ascentcare Dental Labs, Inc., Nunica, Mich., or as disclosed in commonly assigned U.S. Patent Application Publication No. 20160310234, the disclosure of which is incorporated in its entirety herein by reference). The fiber optic cable 110 may be similar to, for example, a fiber optic cable as disclosed in commonly assigned U.S. Patent Application Publication No. 20160310234. The fiber optic cable 110 may include, for example, a polymethyl methacrylate (PMMA) material (e.g., ESKA P/N: GHEV4002). The fiber optic cable 110 may have a refractive index of, for example, 1.49. The fiber optic cable 110 may have a transmission loss of, for example, 170 dB/km. The fiber optic cable 110 may have a bandwidth of, for example, 40 MHz. The fiber optic cable 110 may have a temperature range of, for example, −55° C. to 95° C. The first and second magnetic light couplers 115, 120 may be similar to, for example, a magnetic light coupler as disclosed in commonly assigned U.S. Patent Application Publication No. 20160310234. In fact, the light source 125, the fiber optic cable 110, and the light coupler 115 may be similar to the light delivery system as disclosed in commonly assigned U.S. Patent Application Publication No. 20160310234.

The dental operator room 100 may include a dentist station 135, a dental assistant station 140, a plurality of foot operated switches 130, and at least one wireless battery charger 131 (e.g., an infrared charger, an electromagnetic charger, etc.). The wireless battery charger 131 may be, for example, KIIK as provided by WI-CHARGE LTD., 3 Pekeris St. Rehovot, 7670203, Israel, having a total number of clients 1-50, 24 Wh/day, a total delivered power of 500 mW, a field of view of 100°/100 m$^2$, a maximum transmission distance of 10 m, an output voltage of 5V configurable, and embedded energy storage (e.g., super-capacitor/rechargeable battery). Alternatively, the wireless battery charger 131 may be, for example, KIIK as provided by WI-CHARGE LTD., 3 Pekeris St. Rehovot, 7670203, Israel, having a number of clients 1-10, a total delivered power of 1000 mW, a field of view of 100°/100 m², a maximum transmission distance of 8 m, an output voltage of 5V configurable, and embedded energy storage (e.g., supercapacitor/rechargeable battery). A first one of the plurality of foot operated switches 130 may be configured to, for example, activate the wireless battery charger 131. The wireless battery charger 131 may charge a battery within the light engine 125.

The dentist station 135 and/or the dental assistant station 140 may include a light source 125 and an associated magnetic light coupler 120. A second one of the plurality of foot operated switches 130 may be configured to, for example, activate a first light source 125 (e.g., a visible light emitter 500-700 nm). A third one of the plurality of foot operated switches 130 may be configured to, for example, activate a second light source 125 (e.g., a blue light emitter). The visible light emitter may be used to, for example, illuminate an interior of a dental patient's mouth. The blue light (e.g., 380-500 nm) emitter may be used to, for example, cure an associated blue light curable dental product (e.g., an adhesive, a filler, etc.).

Figure 2A:
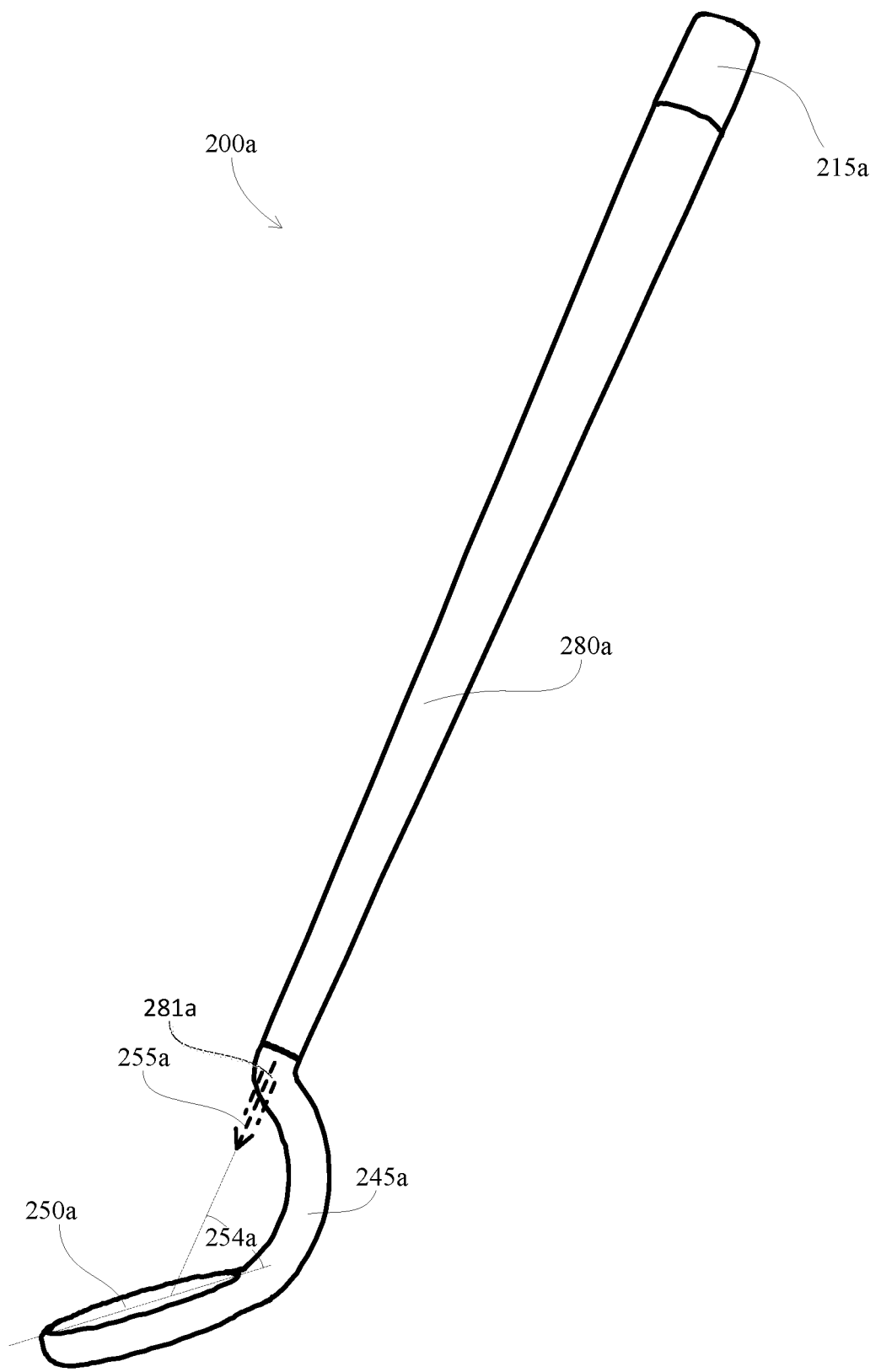
FIGS. 2A-2C depict various views of an example illuminated dental mirror assembly.
Figure 2B:
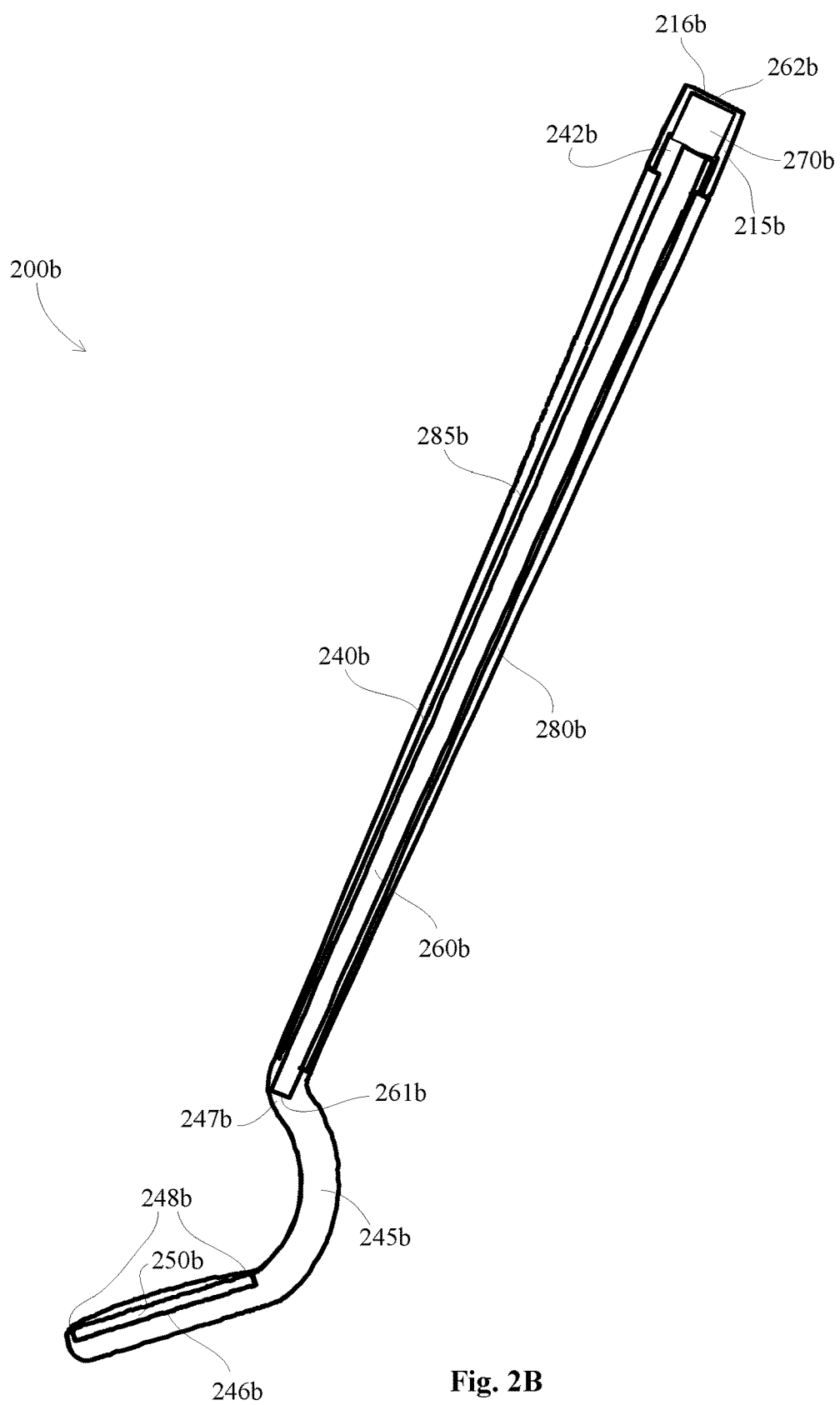
Figure 2C:
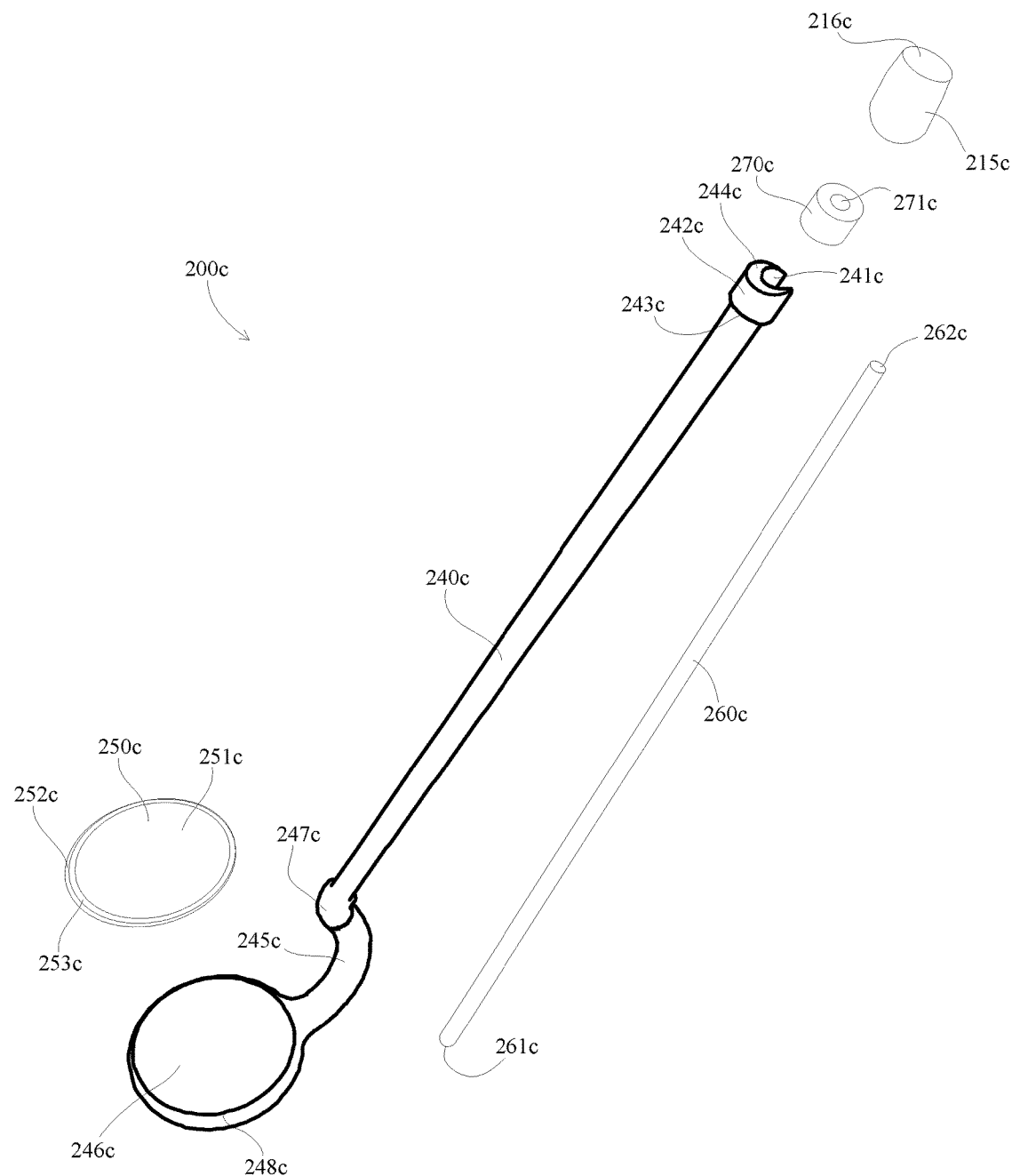
Figure 3A:
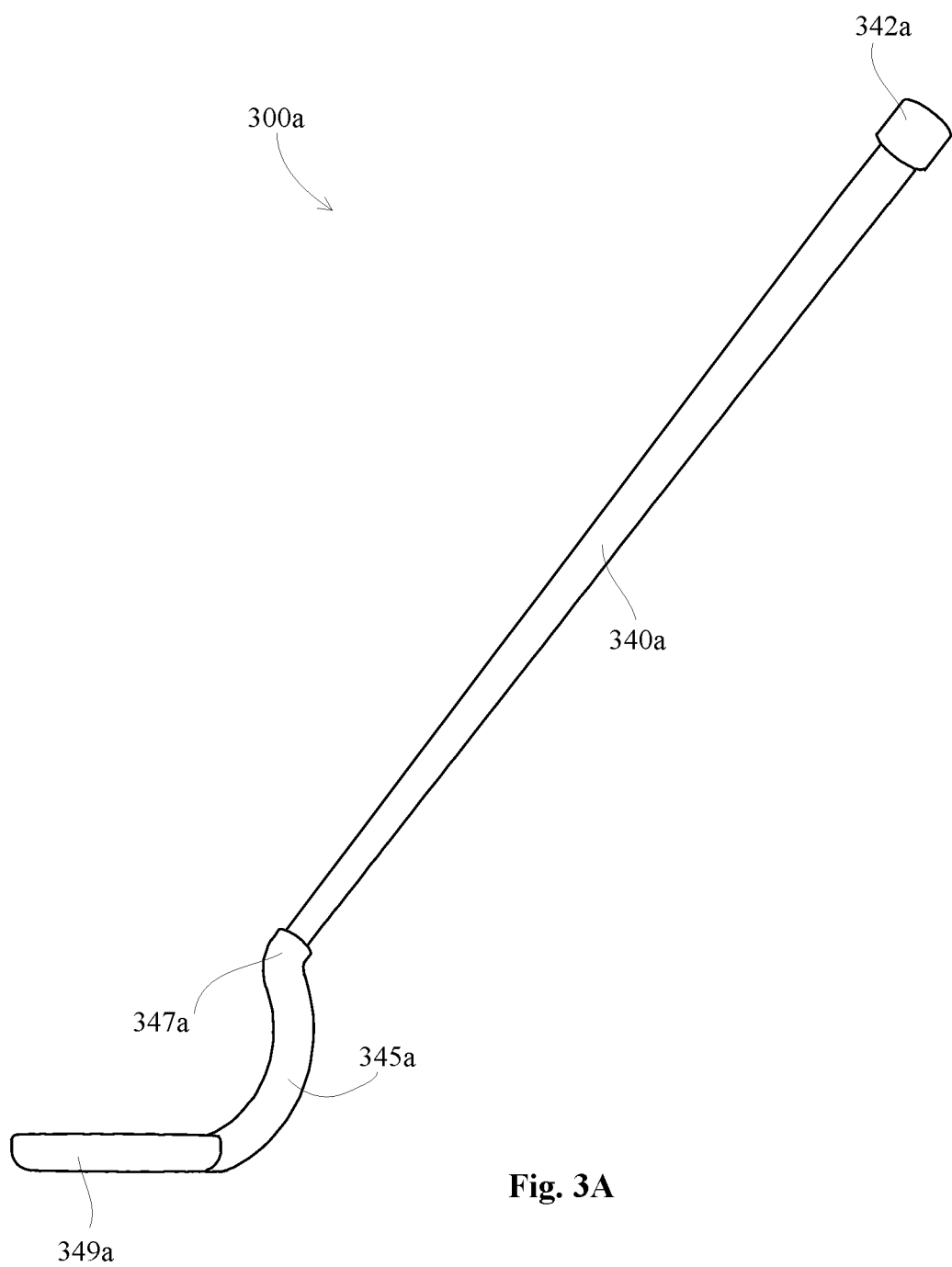
FIGS. 3A-3D depict various views of an example core element for use within the illuminated dental mirror assembly of FIGS. 2A-2C.
Figure 3B:
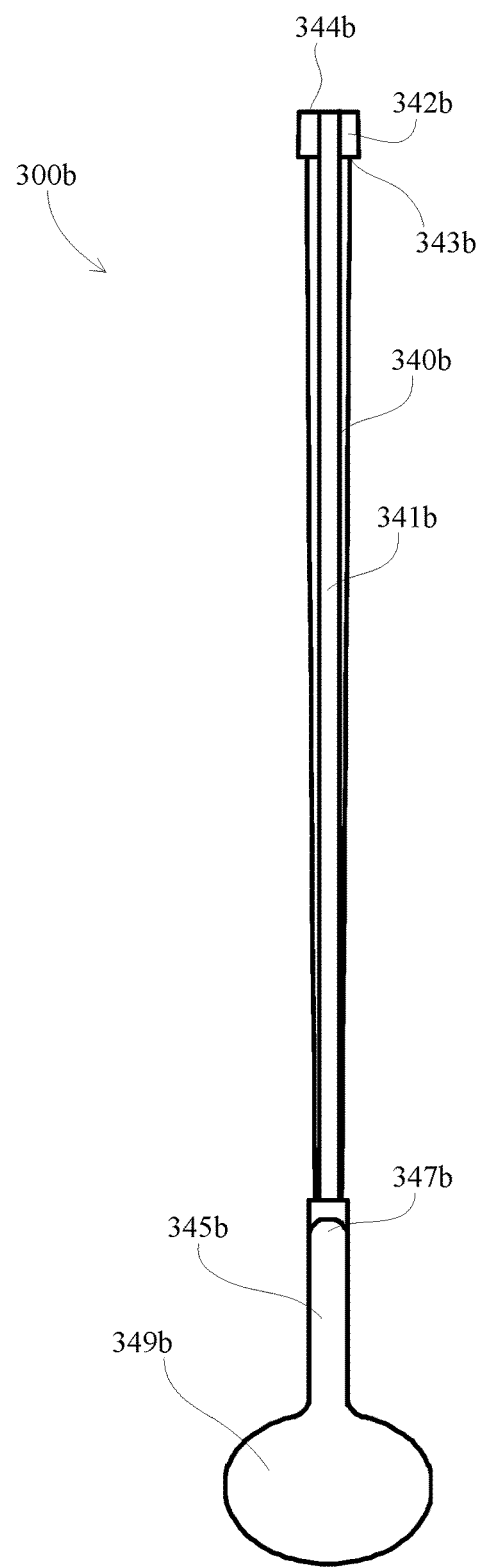
Figure 3C:
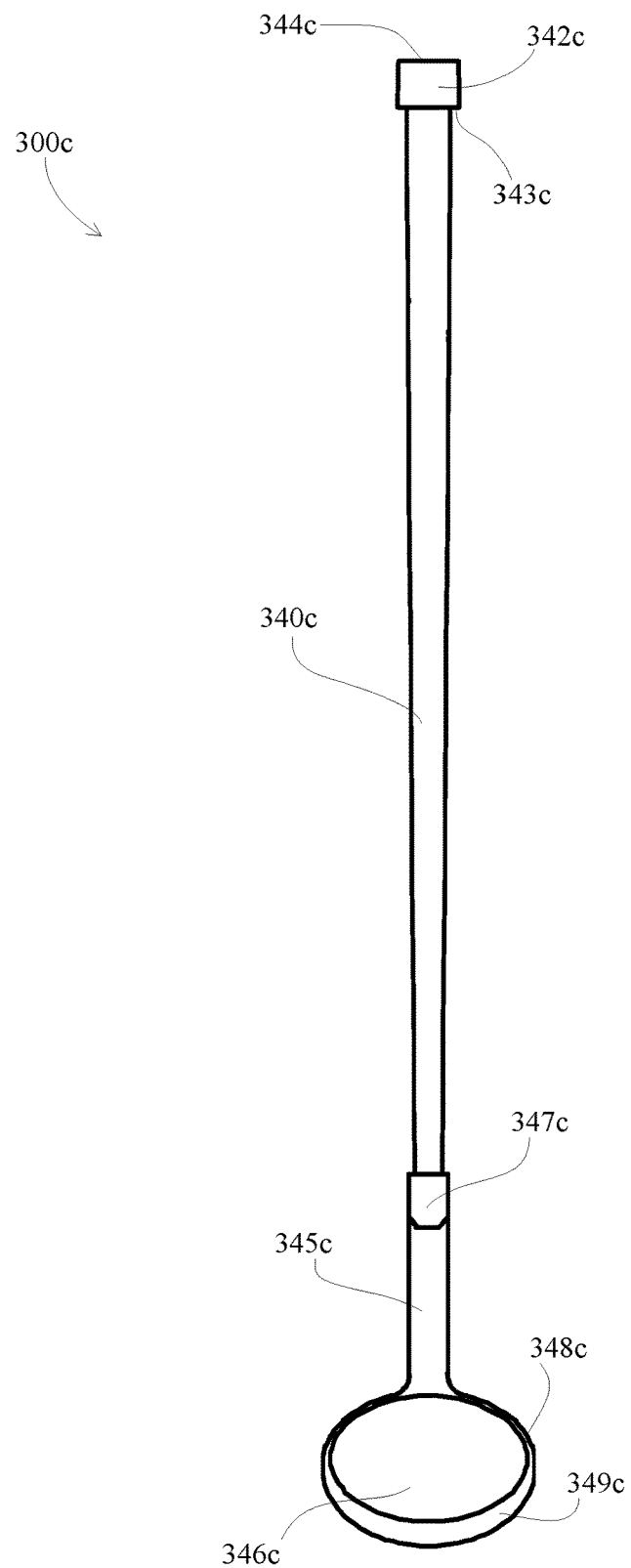
Figure 3D:
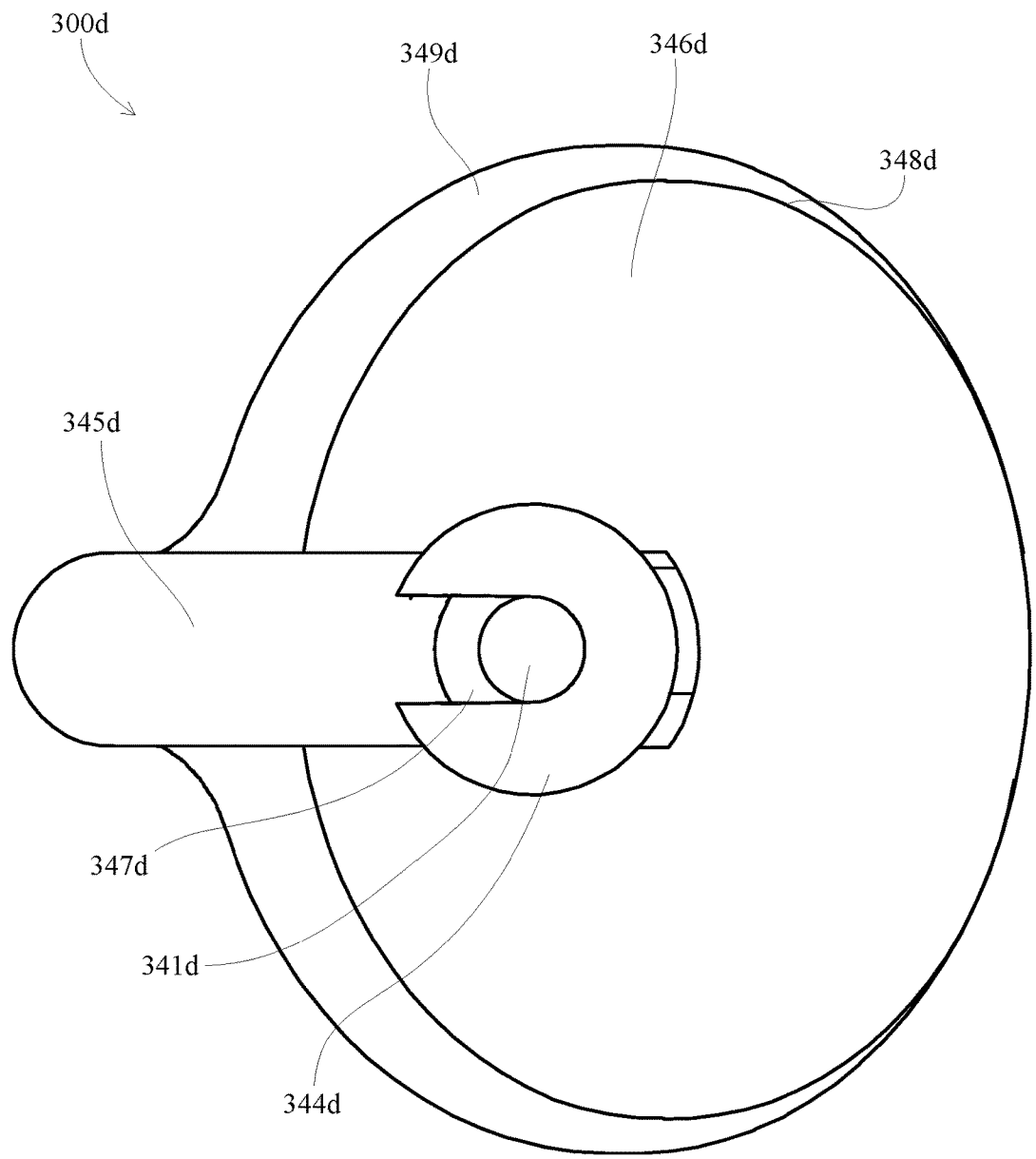

With reference to FIGS. 2A-2C, an illuminated dental mirror assembly 200a-c may include a mirror element 250a-c secured to a handle 280a,b via a mirror element carrier 245a-c. The mirror element carrier 245a-c may be configured to provide a dental patient cheek retractor and/or an illuminated dental patient cheek retractor. The mirror element carrier 245a-c may be at least partially illuminated by, for example, varying a distal end 261b of a fiber optic element 260b to form a desired shape (e.g., hemispherical shape, triangular shape, domed shape, etc.) and/or by selecting a particular adhesive 285b (i.e., an adhesive with a particular refractive index of 1.5 or higher) between the distal end 261b and the mirror element carrier 245a-c. Alternatively, or additionally, at least a portion of the adhesive 285b may be left out between the distal end 261b and the mirror element carrier 245a-c (i.e., forming an air gap between the distal end 261b and the mirror element carrier 245a-c).

The mirror element 250a-c may be, for example, a Crystal HD® mirror as available from Zirc Company, Buffalo, Minn. The handle 280a,b may include, for example, a plastic material (e.g., Maxelast® A9860, as available from Nantong Polymax Elastomer Technolgy, Company, Ltd.). A reflective surface 251c of the mirror element 250a may form an angle 254a with respect to a central axis 281a of the handle 280a. The angle 254a may be, for example, approximately 50°. More generally, the angle 254a may be, for example, between 30° and 60°. Alternatively, the angle 254a may be between 40° and 50°. More broadly, the angle 254a may be selected such that emitted light 255a desirably illuminates an interior of an associated dental patient's mouth and does not undesirably reflect back into an illuminated dental mirror assembly user's eyes. The angle 254a may be selected such that emitted light 255a uniformly illuminates a surface (e.g., surface 251c) of the mirror element 250a-c. The illuminated dental mirror assembly 200a-c may also include an end cap/coupling lens 215a-c. The end cap/coupling lens 215a-c may include, for example, a LEXAN Resin™ HP1 polycarbonate material. The end cap/coupling lens 215a-c may include an index of refraction of, for example, 1.58.

FIG. 2B illustrates a cross section view of an illuminated dental mirror assembly 200b. The mirror carrier 245b includes a mirror element 250b secured within a mirror element receptacle 246b via a circumferentially extending lip 248b via an adhesive (e.g., LOCTITE® AA 3494 P/N: 30765, or AA3922 medical device adhesive, available from Henkel). The mirror carrier 245b may include, for example, a LEXAN Resin™ HP1 material. The mirror carrier 245b may include an index of refraction of, for example, 1.58. The illuminated dental mirror assembly 200b may include a fiber optic element 260b secured within a core element 240b via an adhesive 285b (e.g., LOCTITE® AA 3494 P/N: 28367, available from Henkel). The adhesive 285b may have an index of refraction of, for example, 1.48 to 1.55. The core element 240b may include, for example, a LEXAN Resin™ HP1 material. The core element 240b may include an index of refraction of, for example, 1.58. The fiber optic element 260b may include, for example, a polymethyl methacrylate (PMMA) material (e.g., ESKA P/N: GHEV4002). Alternatively, the fiber optic element may include a glass tube or glass fiber. The fiber optic element 260b may have a refractive index of, for example, 1.50 or higher with a fluorinated polymer (e.g., polytetrafluoroethylene (PTFE)) cladding with a refractive index of 1.49. The fiber optic element 260b may have a transmission loss of, for example, 170 dB/km. The fiber optic element 260b may have a bandwidth of, for example, 40 MHz. The fiber optic element 260b may have a temperature range of, for example, −55° C. to 85° C. The fiber optic element 260b may include a proximal end 262b and a distal end 261b. The proximal end 262b of the fiber optic element 260b may extend through a center aperture of a magnetically energetic element 270b (e.g., a magnetic material, a ferrous metal, a ferrous metal alloy, ferromagnetic material, a permanent magnet, a neodymium (NdFeB) high curie temperature ($T_c$) magnetic material, etc.) to receive light through a light transmission surface 216b of an end cap/coupling lens 215b. The magnetically energetic element 270b may be, for example, axially magnetized, high-temperature, nickel plated neodymium (NdFeB). The magnetically energetic element 270b may be ¼" O.D., ¼" height, and have a ⅛" I.D. aperture. Light, received at the proximal end 262b of the fiber optic element 260b, may propagate through the fiber optic element 260b to the distal end 261b of the fiber optic element 260b. Light may be emitted through a light emitting portion 247b of the illuminated dental mirror 200b (i.e., as illustrated by light rays 255a of FIG. 2A). The distal end 261b may be formed to a desired shape (e.g., hemispherical shape, triangular shape, domed shape, etc.) to emit a desire pattern of light rays 255a.

The adhesive 285b may extend between the proximate end 262b of the fiber optic element 260b and the end cap/coupling lens 215b. The adhesive 285b may extend between the distal end 261b of the fiber optic element 260b and the light emitting portion 247b of the illuminated dental mirror 200b (i.e., as illustrated by light rays 255a of FIG. 2A). Light may travel through the surface 216b of the end cap/coupling lens 215b (index of refraction 1.58), through the adhesive 285b (index of refraction 1.49 or higher), through the fiber optic element 260b (index of refraction 1.50 or higher) with a PTFE or silicone cladding with a refractive index of 1.46, through the adhesive 285b (index of refraction 1.50 or higher), and exit the light emitting portion 247b (index of refraction 1.58) of the illuminated dental mirror 200b. Adhesive 285b may reduce undesirable light refraction, scattering, and/or reflection compared to, for example, having an air gap (index of refraction 1.0) between the proximate end 262b of the fiber optic element 260b and the end cap/coupling lens 215b and/or between the distal end 261b of the fiber optic element 260b and the light emitting portion 247b.

The end cap/coupling lens 215b may be secured to a cap post 242b of the core element 240b. The illuminated dental mirror assembly 200b may include an encapsulate material 280b that may encapsulate the portion of the fiber optic element 260b and the core element 240b that extends between the end cap/coupling lens 215b and the mirror element carrier 245b. The encapsulate material 280b may include, for example, a plastic material (e.g., Maxelast® A9860, as available from Nantong Polymax Elastomer Technolgy, Company, Ltd.).

FIG. 2C illustrates an exploded view of an illuminated dental mirror assembly 200c. The illuminated dental mirror assembly 200c may include a core element 240c having a mirror element carrier 245c, a fiber optic element channel 241c, and an end cap post 242c having an inward facing surface 243c and an outward facing surface 244c. The mirror element carrier 245c may include a mirror element receptacle 246c having a circumferentially extending lip 248c configured to, for example, secure a mirror element 250c within the mirror element receptacle 246c. The core element 240c may include a light emitting portion 247c.

The mirror element 250c may include a reflective material 251c (e.g., silver, silver with an indium-tin oxide overcoat, chromium, aluminum, silver-gold alloy, zirconium, zirconium alloy, etc.) extending over a beveled edge 253c. The reflective material 251c may also extend over a peripheral edge 252c. The circumferentially extending lip 248c may mate with the beveled edge 253c to secure the mirror element 250c within the mirror element receptacle 246c.

The illuminated dental mirror assembly 200c may include a fiber optic element 260c having a proximal end 262c and a distal end 261c, a magnetically energetic material 270c having an aperture 271c, and an end cap/coupling lens 215c having a light transmission surface 216c.

In an alternative configuration, an illuminated dental mirror assembly 200a-c may include, for example, a handle 280a, 280b and a mirror element carrier 245a-c formed of a metallic material (e.g., stainless steel) with a fiber optic element 260b, 260c within a longitudinally extending aperture of the handle 280a, 280b. An end cap/coupling lens 215a-c may be adhered to a proximate end of the handle 280a, 280b and a light emitting portion 247b (e.g., a light emitting optic) may be adhered to a distal end of the handle 280a, 280b to encapsulate the fiber optic element 260b, 260c within the illuminated dental mirror assembly 200a-c.

Turning to FIGS. 3A-3D, an illuminated dental mirror assembly 300a-d may include a core element 340a-c. The core element 340a-c may include a mirror element carrier 345a-d, a fiber optic element channel 341b, 341d, and an end cap/coupling lens post 342a-c having an inward facing surface 343b, 343c and an outward facing surface 344b-d. The mirror element carrier 345a-d may include a light emitting portion 347a-d, a mirror element receptacle 346c, 346d, a circumferentially extending lip 348c, 348d, and a mirror element receptacle perimeter portion 349a-d. The mirror element receptacle 346c may be trans-illuminated. Additionally, or alternatively, the mirror element receptacle 346c may be configured as a dental patient tongue depressor.

With reference to FIGS. 4A-4C, an illuminated dental mirror assembly 400a-c may include an end cap/coupling lens 415a-c. The end cap/coupling lens 415a-c may include a light transmitting surface 416a-c, a magnetically energetic material/end cap/coupling lens post receptacle 417a-c, and an inward facing surface 418a-c. When the end cap/coupling lens 415a-c is incorporated within an illuminated dental mirror assembly 400a-c, a magnetically energetic material (e.g., magnetically energetic material 270b, 270c) may be inserted into the magnetically energetic material/end cap/coupling lens post receptacle 417a-c and the end cap/coupling lens 415a-c may be secured over an end cap/coupling lens post (e.g., end cap/coupling lens post 242b, 242c, 342a-c) such that the inward facing surface 418a-c is substantially aligned with an inward facing surface (e.g., inward facing surface 243c, 343b, 343c) of the end cap/coupling lens post 242b, 242c, 342a-c, and the magnetically energetic material 270b, 270c is proximate an outward facing surface (e.g., outward facing surface 244c, 344b-d).

Figure 5A:
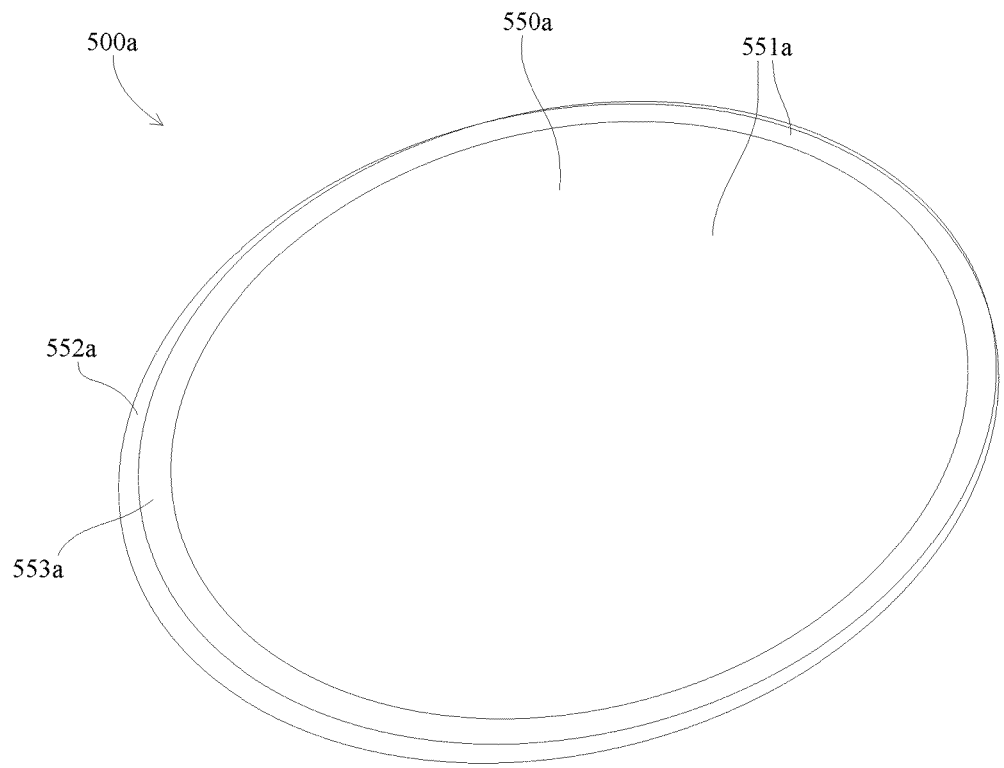
FIGS. 5A and 5B depict various views of an example mirror element for use within the illuminated dental mirror assembly of FIGS. 2A-2C.
Figure 5B:
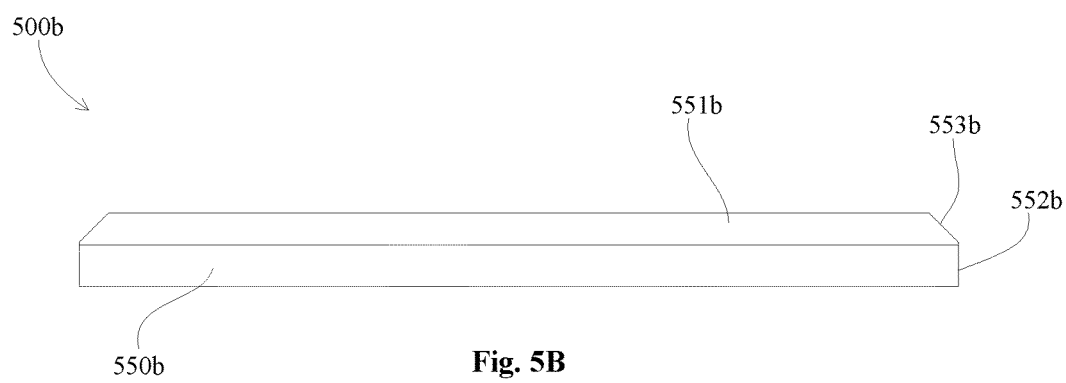

Turning to FIGS. 5A and 5B, an illuminated dental mirror assembly 500a,b may include a mirror element 550a,b. The mirror element 550a, b may include a reflective material 551a,b (e.g., silver, silver with an indium-tin oxide overcoat, chromium, aluminum, silver-gold alloy, zirconium, zirconium alloy, etc.) extending over a beveled edge 553a,b. The reflective material 551a,b may also extend over a peripheral edge 552a,b.

Figure 6A:
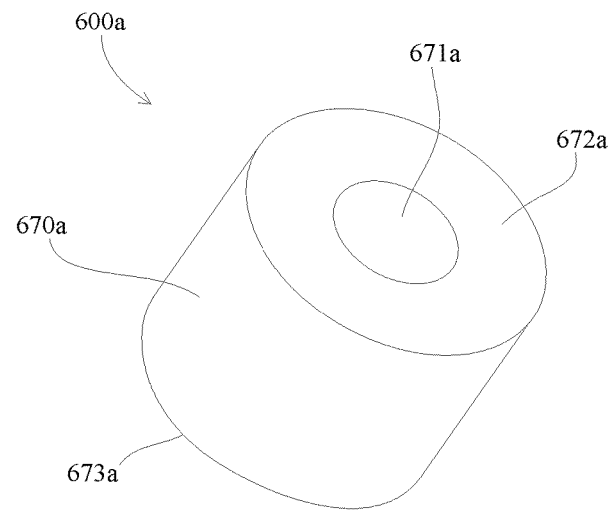
FIGS. 6A-6C depict various views of an example magnetically energetic element for use within the illuminated dental mirror assembly of FIGS. 2A-2C.
Figure 6B:
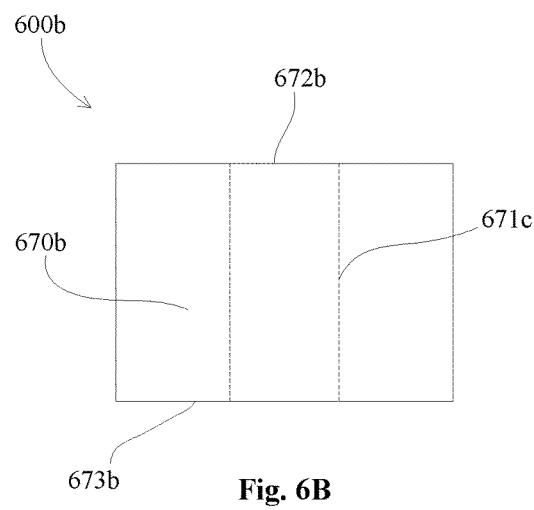
Figure 6C:
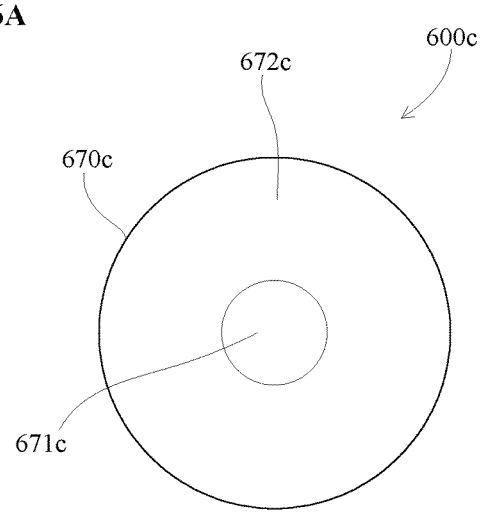

With reference to FIGS. 6A-6C, a magnetically energetic material for use in an illuminated dental instrument assembly 600a-c may include a magnetically energetic element 670a-c (e.g., a magnetic material, a ferrous metal, a ferrous metal alloy, ferromagnetic material, a permanent magnet, a neodymium (NdFeB) high curie temperature ($T_c$) magnetic material, etc.). The magnetically energetic material 670a-c may include an inward facing surface 673a, an outward facing surface 672a-c, and an aperture 671a-c extending through the magnetically energetic material 670a-c from the outward facing surface 672a-c to the inward facing surface 673a-c.

A handle may be constructed from latex-free material and may be comprised of polypropylene formed via a first injection molding process. A handle may include santoprene thermoplastic vulcanizates (TPV) via a second injection molding process. The second injection molding process may allow creation of a structure that provides protection for the first magnetically energetic material and the fiber optic element. An illuminated dental mirror assembly for larger patients may include larger component size that may be desirable. For smaller patients and for children, a smaller pediatric size illuminated dental mirror may be desirable. For those patients of medium or moderate build, a medium or various intermediate size illuminated dental mirror may be provided to provide desired comfort for any particular patient.

Dental instruments (e.g., illuminated dental mirrors, illuminated dental wedges, illuminated dental picks, illuminated dental bite blocks, etc.) may be subject to repeated sterilization (e.g., autoclaving, etc.) at temperatures exceeding 180° F. for extended periods of time in order to sterilize the dental instruments for subsequent use. A permanent magnetic material, that is susceptible to reduction of its magnetic properties at high temperatures, may, therefore, be undesirable.

Figure 7A:
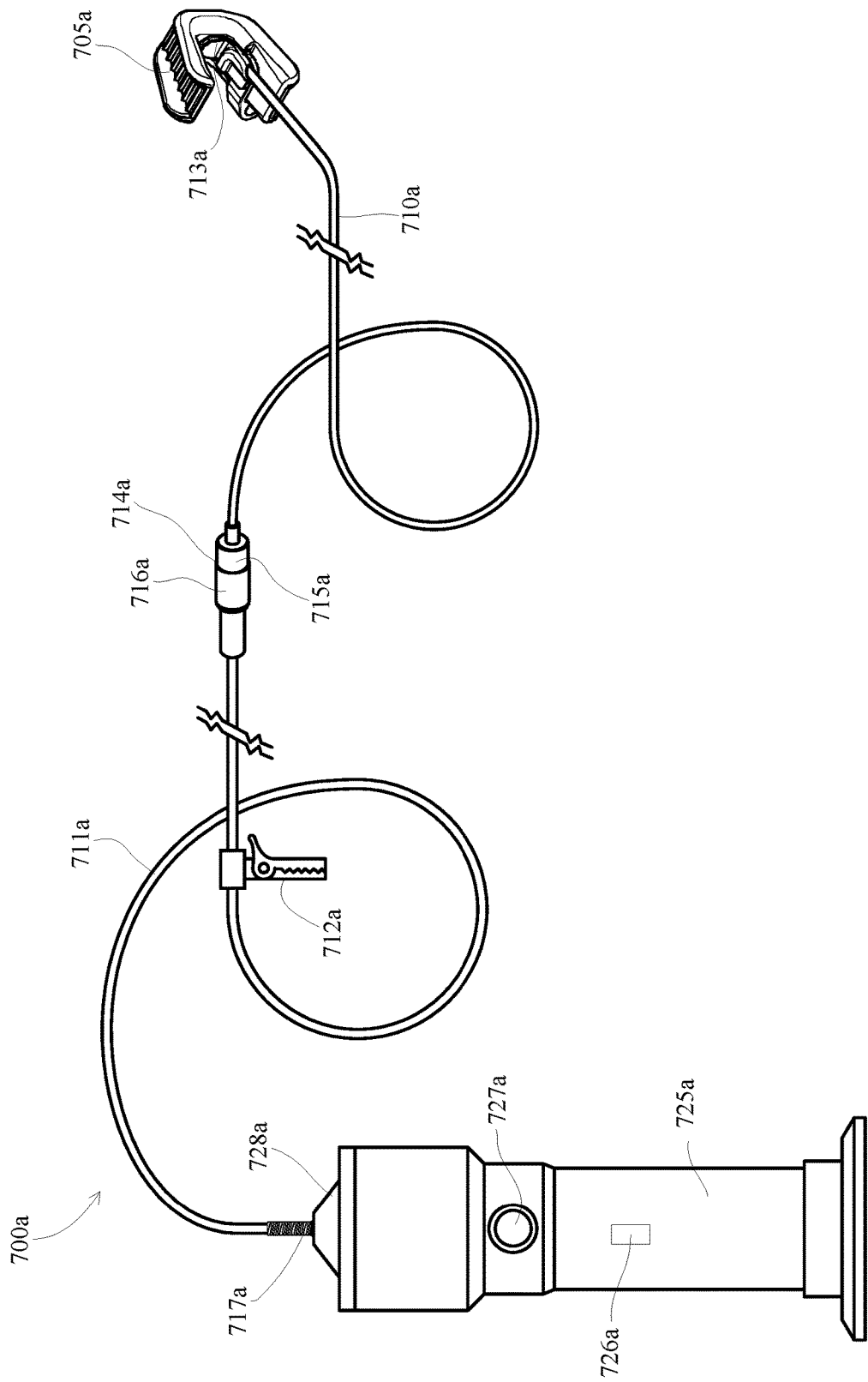
FIGS. 7A and 7B depict various views of an example light engine assembly.
Figure 7B:
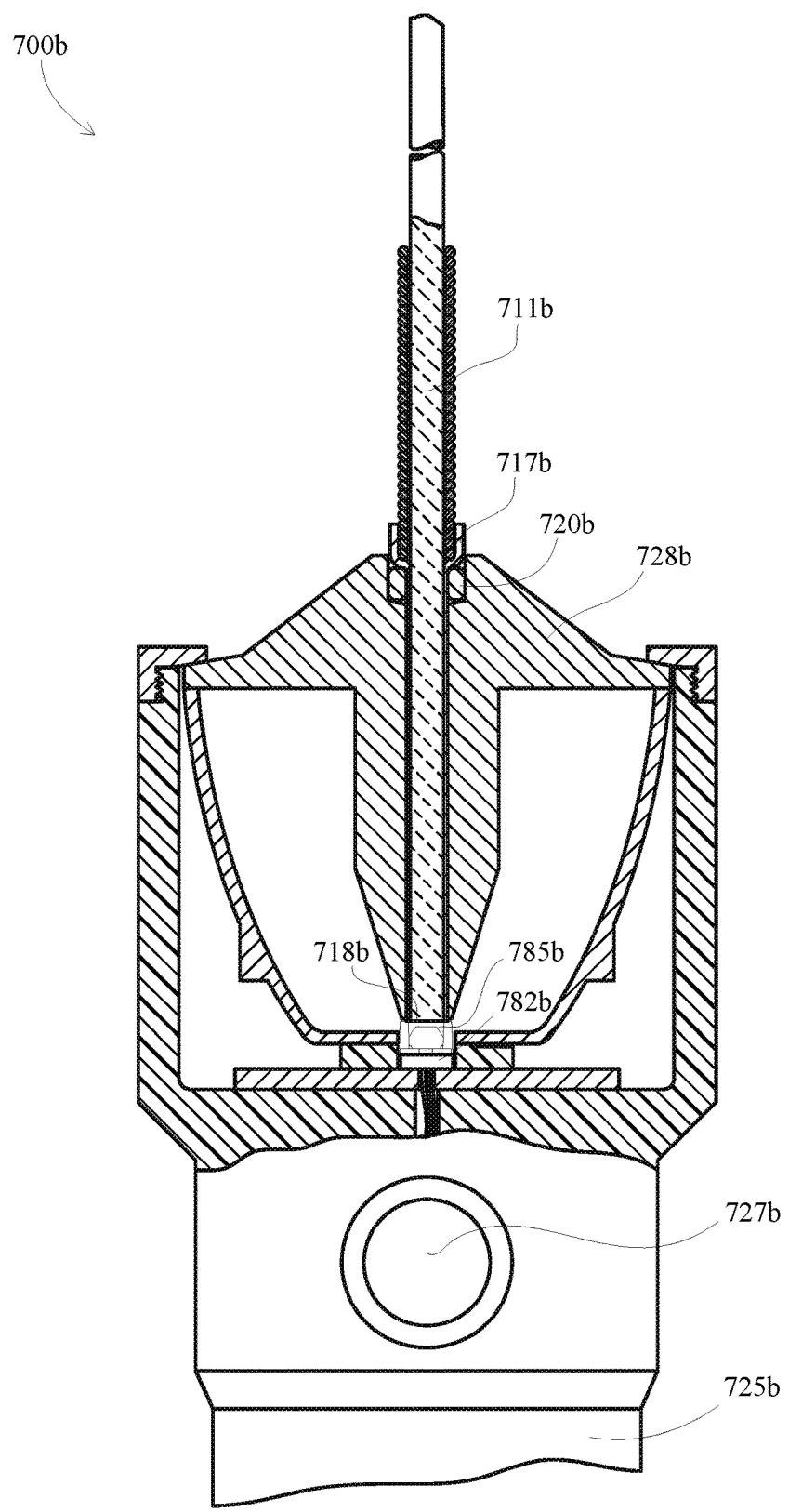

Turning to FIGS. 7A and 7B an example light engine assembly 700a,b may include a light engine 725a,b (e.g., Model No. HYLUX-STM-B as available from Ascentcare Dental Products, Inc., Nunica, Mich.). This light engine 725a,b may include a light emitting diode light source 782b (e.g., Cree XP-L HI LED) with, for example, a maximum output of 1100 lumens. The light engine 725a,b may offer three brightness levels, for example, 1100 lumens, 550 lumens, and 80 lumens selectable via a multi-stage push-button 727a,b. As the light engine 725a,b may develop a significant amount of heat, the light engine 725a,b may include an aluminum heat dissipater 728a,b having an upper end and a lower end. The aluminum heat dissipater 728a,b may maintain the light engine 725a,b at 120° F. or lower to maintain a high level of light generated for long periods of time, for example, 20 to 40 minutes. Thermal management may enable maintaining a high level of light output, while also reducing thermal exposure to associated batteries, fiber optic light cable 711a,b, and preventing component and battery failure.

The upper end of the aluminum heat dissipater 728a,b may be fabricated from 6061 grade aluminum and may be readily machined into the shape shown in FIG. 7B, and may be formed with a collar that extends concentrically about the aluminum heat dissipater 728a,b and may be supported by an upper edge of an associated reflector of the light engine 725a,b. A threaded ring, which is normally used to retain a tempered glass lens against the reflector in an unmodified light engine 725a,b, may be reinstalled to secure and sealingly mount the aluminum heat dissipater 728a,b in position, where the collar preferably has a thickness that is substantially the same as the discarded tempered glass lens, as shown in FIG. 7B.

The lower end of the aluminum heat dissipater 728a,b may be positioned proximate a bottom opening at the base of the reflector and within a few millimeters, preferably 2 mm, of the LED 782b of the light engine 725a,b. A passage may be machined through the aluminum heat dissipater 728a,b and may form a throughway between an opening at the upper end of the aluminum heat dissipater 728a,b proximate the bottom opening at the base of the reflector and an opening at the lower end of the aluminum heat dissipater 728a,b. A countersunk cavity may be formed at the upper end of the aluminum heat dissipater 728a,b concentric with the opening within which a magnet 720b having an axial concentric opening may be received and affixed.

An exposed first distal end 718b of a fiber optic cable 711a,b may extend through and may be fixedly restrained within a removable conduit, preferably fabricated from a large stainless steel hypodermic needle. The outer diameter of the removable conduit may be slightly smaller than the inner diameter of the passage within the aluminum heat dissipater 728a,b, whereby the removable conduit may be fittingly and slidingly received within the passage. A short length of the fiber optic cable 711a,b may extend beyond a lower portion of the removable conduit. The fiber optic cable 711a,b may be comprised of 2 mm solid core side glow fiber optic cable fabricated of PMMA. The fiber optic cable 711a,b may be approximately 3 meters long in order to allow maximum flexibility of its application. An upper portion of the removable conduit may be provided with a clamp that may extend around an outer circumference of the fiber optic cable 711a,b and may be mechanically crimped (preferably in an octagonal pattern) into position to fixedly restrain the first distal end 718b of the fiber optic cable 711a,b within the removable conduit. The clamp may be fabricated from a magnetic or a ferromagnetic material 717a,b so as to be attracted to the magnet 720b. Thus, when the removable conduit is fully inserted within the passage of the aluminum heat dissipater 728a,b, the magnet 720b and the clamp 717a,b may cooperate to restrain the removable conduit and the exposed first distal end 718b of the fiber optic cable 711a,b in position. Alternatively, a collet (not shown) may be attached to a threaded conical flange (not shown) on the upper end of the aluminum heat dissipater 728a,b through which the first distal end 718b of the fiber optic cable 711a,b may pass and may be secured.

Thus, the exposed first distal end 718b of the fiber optic cable 711a,b may be disposed within the bottom opening and proximate the lower end of the aluminum heat dissipater 728a,b proximate a lens 785b. The exposed first distal end 718b of the fiber optic cable 711a,b may be positioned, for example, 2 mm away from the lens 785b and the lens 785b may be, for example, 2 mm away from the LED light source 782b. The supply fiber optic cable 711a,b may be passed through the passage within the aluminum heat dissipater 728a,b and may exit the upper end of the aluminum heat dissipater 728a,b via an associated opening. A strain relief spring may be likewise mechanically coupled with the clamp/magnet 717b and may be disposed about a portion of the fiber optic cable 711a,b as it exits the opening of the upper end of the aluminum heat dissipater 728a,b, which may prevent the fiber optic cable 711a,b from bending at a small radius (e.g., a radius less than a 15 mm radius) and, thereby, may prolong fiber optic cable 711a,b life.

By virtue of the cooperation between the magnet 720b and clamp/magnet 717a,b, a strain relief spring and the fiber optic cable 711a,b may be allowed to rotate 360° relative the vertical axis of the aluminum heat dissipater 728a,b, so as to prevent tangling and binding of the fiber optic cable 711a,b while it is in use. In addition, removal of the removable conduit from the passage and reinsertion of the removable conduit into the passage can be simply and readily accomplished with one-hand operation of the user. When so reinserted, the exposed first distal end 718b of the fiber optic cable 711a,b may be precisely positioned over the lens 785b and the LED 782b.

The LED 782b may generate a significant amount of heat energy and the aluminum heat dissipater 728a,b may be useful in forming a pathway for this heat energy to flow from the LED 782b and its associated components to the environment. The aluminum heat dissipater 728b may be assembled to the light engine 725a,b with a thermal grease (sometimes referred to as CPU grease, heat paste, heat sink compound, heat sink paste, thermal compound, thermal gel, thermal interface material, thermal paste, or grey goo) to provide a thermally conductive (but usually electrically insulating) interface. Such an interface is commonly used between heat sinks and heat sources, for example, in high-power semiconductor devices. The thermal grease is believed to eliminate air gaps or spaces, which act as a thermal insulator, from the interface area so to maximize heat transfer. This promotes a heat energy flow path away from the LED 782b and light engine 728a,b to reduce temperatures.

An opposite second distal end 715a of the supply fiber optic cable 711a,b may be attached to a magnetic light coupler 716a. The magnetic light coupler 716a may include a first half and a second half, where the first half may comprise, for example, an aluminum cylindrical body having an open cylindrical cavity having an inner diameter and a circular base proximate the open cylindrical cavity within which is mounted a permanent magnet. The cylindrical body may be coupled with the second distal end 715a of the fiber optic cable 711a,b via a sheath assembly, the sheath assembly may have an enlarged portion having an outer diameter similar to the outer diameter of the circular base and disposed proximate the permanent magnet, about which both the cylindrical body may be molded and encapsulated.

The permanent magnet and the circular base may each be provided with a concentric opening through and within which the opposite second distal end 715a of the fiber optic cable 711a,b may be received, wherein a face of the second distal end 717a of the fiber optic cable 711a,b may be fully exposed. The second distal end 715a of the fiber optic cable 711a,b may be clamped in situ via the sheath assembly and may be prevented from separating from the first half of the magnetic light coupler 716a. The permanent magnet and second distal end 715a of the fiber optic cable 711a,b may be encased in, for example, a clear plastic, or polycarbonate, to permanently secure the permanent magnet therein and to otherwise enclose the second distal end 715a of the fiber optic cable 711a,b, while maintaining an exposed face at the second distal end 715a of the fiber optic cable 711a,b.

An alligator clip 712a, for example, may be attached to the sheath assembly, whereby the first half of the magnetic light coupler 716a can be readily attached to and detached from an article of clothing of the dentist, dental hygienist, and/or patient. Thus, the light engine 725a,b and the first end of the magnetic light coupler 716a can be essentially worn as part of a garment of the dental care provider.

The second half of the magnetic light coupler 716a may comprise a substantially solid cylindrical body having an outer diameter that is slightly smaller than the inner diameter of the open cylindrical cavity of the first half of the magnetic light coupler 716a. The second half of the magnetic light coupler 716a may similarly have a cooperating permanent magnet, and a second distal end of the accessory fiber optic cable 710a,b, opposite the first distal end 715a of the accessory fiber optic cable 710a which may be attached to a light mount encapsulated within and permanently attached to the solid cylindrical body of the second half of magnetic light coupler 716a. The permanent magnetic may similarly have a concentric opening within which the second distal end of the accessory fiber optic cable 710a may be received and through which the second distal end of the accessory fiber optic cable 710a may be received and mounted.

The solid cylindrical body of the first half of the magnetic light coupler 715a may be received within the open cylindrical cavity of the second half of the magnetic light coupler 716a to assemble the magnetic light coupler 714a. Preferably, an abutting face of the second half of the magnetic light coupler 716a may have approximately a 1 mm thick, optically clear UV-cured resin disposed thereon that fully encapsulates the second distal end of the accessory fiber optic cable 710a. A pair of crimp rings may be disposed about and mechanically crimped against the outer cladding of each of the fiber optic cables 710a, 711a,b and embedded within each of the first and second halves of the magnetic light coupler 716a to prevent separation.

Both permanent magnets may be formed of an axially magnetized neodymium high curie temperature magnet and oriented in complementary pole relationship, so that the S and N poles are disposed in adjacent and abutting relation. Thus, when the solid cylindrical body of the first half of the magnetic light coupler 715a is inserted within the open cylindrical cavity of the second half of the magnetic light coupler 716a, the respective exposed second distal end of the fiber optic cable 711a,b may be brought into juxtaposed relationship with second distal end of accessory fiber optic cable 710a by the mutual attraction of the permanent magnets in the first and second ends of the magnetic light coupler 714a so as to allow the transmission of light from the light engine 725a,b, through the fiber optic cable 711a,b to the accessory fiber optic cable 710a, and ultimately to the dental instrument assembly 705a,b (e.g., illuminated dental bite block, illuminated dental mirror, illuminated dental wedge, illuminated dental pick, etc.). A coupling force may be approximately 2-4 pounds force to separate the first 715a and second 716a ends of the magnetic light coupler 714a. This may provide a relatively secure connection between the first 715a and second 716a halves of the magnetic light coupler 714a to prevent inadvertent separation of the two, while at the same time allows the user to readily separate the magnetic light coupler 714a intentionally when desired. As noted above, preferably the second half 716a of the magnetic light coupler 714a may be fully encased within an optically clear UV-cured resin. This is particularly advantageous in that, by so doing, the entire accessory fiber optic cable 710a may be adapted for use in an autoclave machine for sterilization of the second fiber optic cable, including the dental accessory 705a at the first distal end of the accessory fiber optic cable 710a and the second half 715a of the magnetic light coupler 714a at the second distal end of the accessory fiber optic cable 710a, as has been noted herein. Further, the dentist and/or dental hygienist need carry only the light engine 725a,b and the fiber optic cable 711a,b attached thereto on their person and to then proceed from patient to patient, without needing to disassemble or sterilize the light engine 725a,b and fiber optic cable 711a,b attached thereto. Rather, only the accessory fiber optic cable 710a, which can be readily disconnected from the fiber optic cable 711a,b as described above, need be sterilized. The fiber optic cables 710a, 711a,b should be sufficiently long so as to provide movement of the dentist and dental hygienist without inadvertently disconnecting the magnetic light coupler 714a.

This arrangement for providing a light engine 725a,b entirely separate than the dental instrument assembly 705a situated within the patient's mouth has been found to be very advantageous. Particularly in the context of the heat developed with other light sources, such as a light source mounted on a headband and disposed on the forehead of the dentist and/or dental hygienist for directing a beam of light into the patient's mouth, the present disclosure offers important advantages in that the heat emitted by the light source on the forehead of the dentist and/or dental hygienist is simply not present. Additionally, the dentist and/or dental hygienist need not worry about carrying around additional batteries to replace batteries that may go dead during use.

A further benefit of using polycarbonate materials in conjunction with the light engine is that a ultraviolet (UV) and/or blue light blocker additive can be incorporated such that the polycarbonate plastic may filter UV and/or blue light radiation. The dental profession has recently moved toward use of blue light curable resins to adhere dental appliances to a patient's mouth. Thus, it is often desirable that light being introduce inside a dental patient's mouth not contain UV or blue light radiation, and that the dentist and and/or dental hygienist be provided with the highest level of control over the application of UV and blue light radiation to a dental patient.

In a further feature of the present disclosure, an optical fiber inspection filament (e.g., fiber optic element 1110a of FIG. 11A) can be provided. Such an inspection filament 1110a, may comprise a 0.5 mm-1.0 mm fiber optic cable which, for example, may be fabricated from PMMA, and may be free at a first distal end for insertion into a patient's mouth. The first distal end may be completely exposed to allow full transmission of light from the light engine 725a,b, through the fiber optic cable 711a,b and the inspection filament 1110a, to provide intense light within the patient's mouth. Because the inspection filament 1110a may be highly flexible, the inspection filament 1110a may be manipulated by a dentist and/or dental hygienist to illuminate and allow inspection anywhere within the patient's mouth. Thus, the dentist and/or dental hygienist can look behind the patient's teeth and obtain a visual inspection of enamel and structures of the patient's teeth. Alternatively, or additionally, the dentist and/or dental hygienist can illuminate the patient's teeth from behind, and obtain a visual inspection of the enamel and structures of an interior of the patient's teeth.

The light engine 725a,b may include a battery charger receptacle 726a configured to plug into, for example, a standard 12 Vdc battery charger. The battery charger receptacle 726a may be configured to plug into any other electric power source (e.g., a 120 Vac source when, for example, the light engine 725a,b includes an integral 120 Vac/12 Vdc power supply).

Figure 8A:
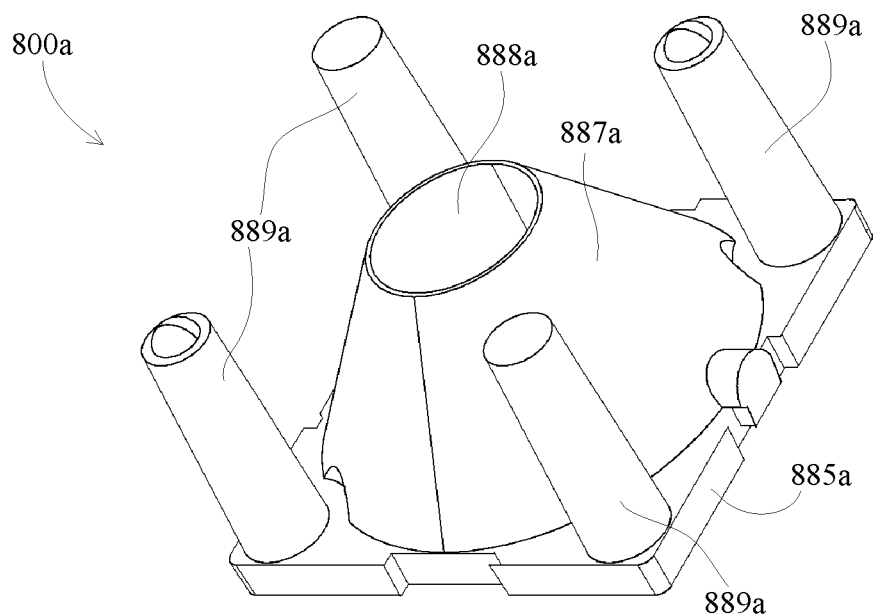
FIGS. 8A and 8B depict various views of an example lens for use within a light engine.
Figure 8B:
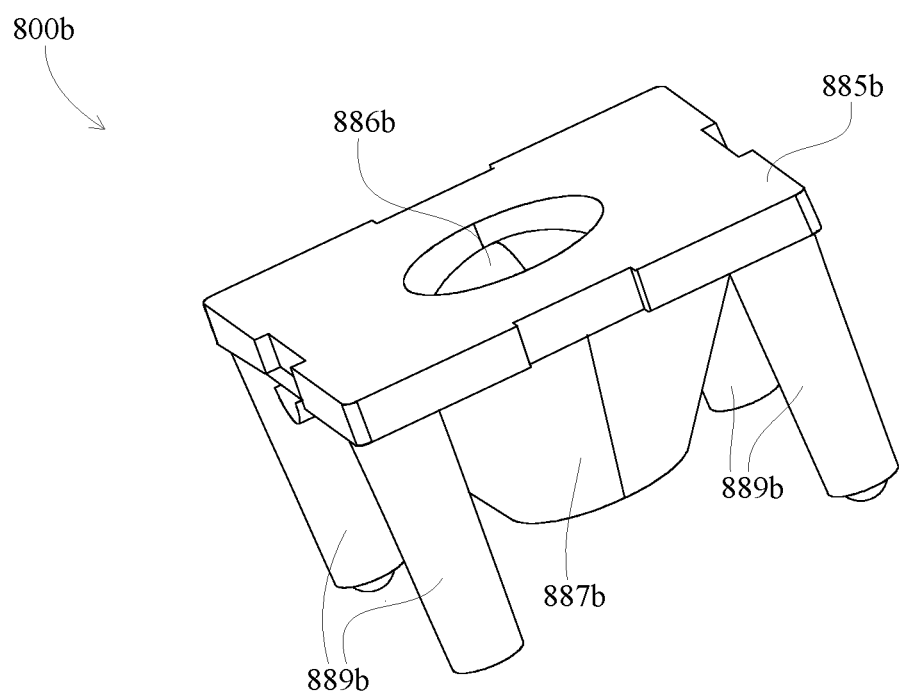

With reference to FIGS. 8A and 8B, a lens 800a,b may be configured for use within a light engine 125, 725a,b. The lens 800a, b may be similar to, for example, the lens 785b of FIG. 7B. The lens 800a,b may include a light collecting optic 886b and a light collimating optic 887a,b extending from opposite sides of a body 885a,b. The lens 800a, b may include a fiber optic cable receiving aperture 888a and alignment posts 889a,b. As illustrated in FIG. 7B, the lens 785b, 800a,b may be positioned within an associated light engine 725b with the light collecting optic 886b proximate a light source (e.g., LED 782b) and with the light collimating optic 887a,b oriented toward an end 718b of a fiber optic cable 711b. The lens 800a,b may, for example, amplify LUX transmitted through the fiber optic cable 711b from 40,000 LUX without the lens 800a,b to 120,000 LUX with the lens 800a,b.

Figure 9A:
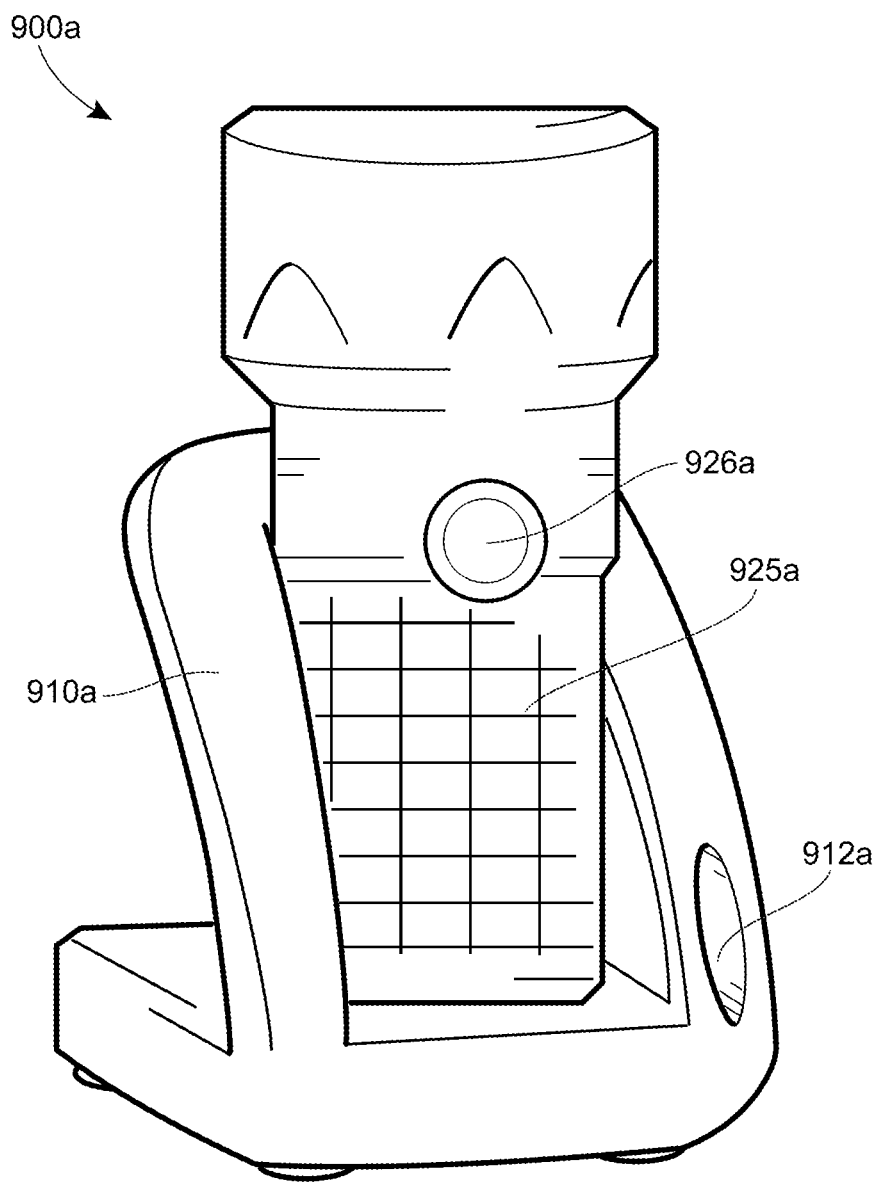
FIGS. 9A-9C depict various views of an example cradle assembly.
Figure 9B:
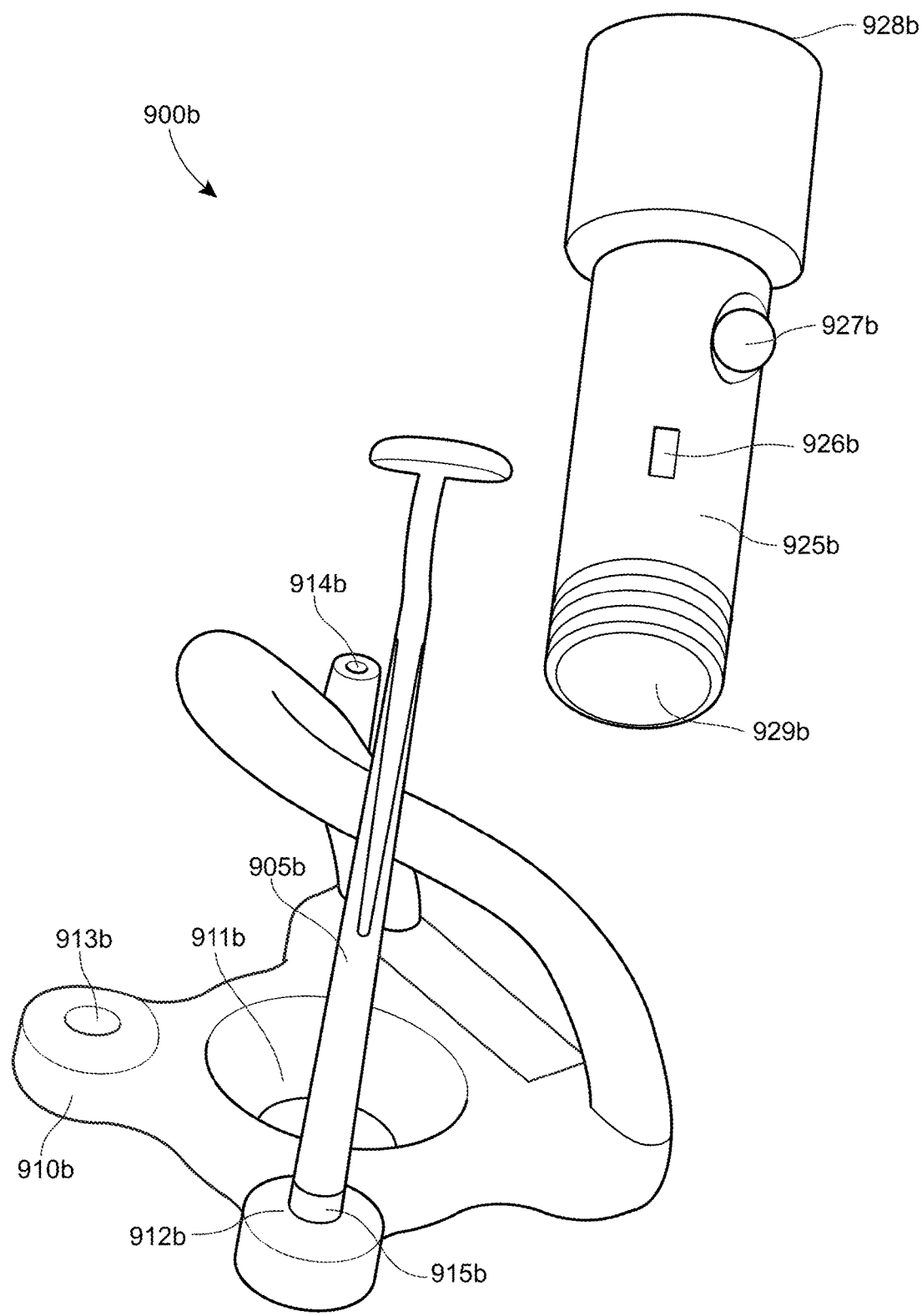
Figure 9C:
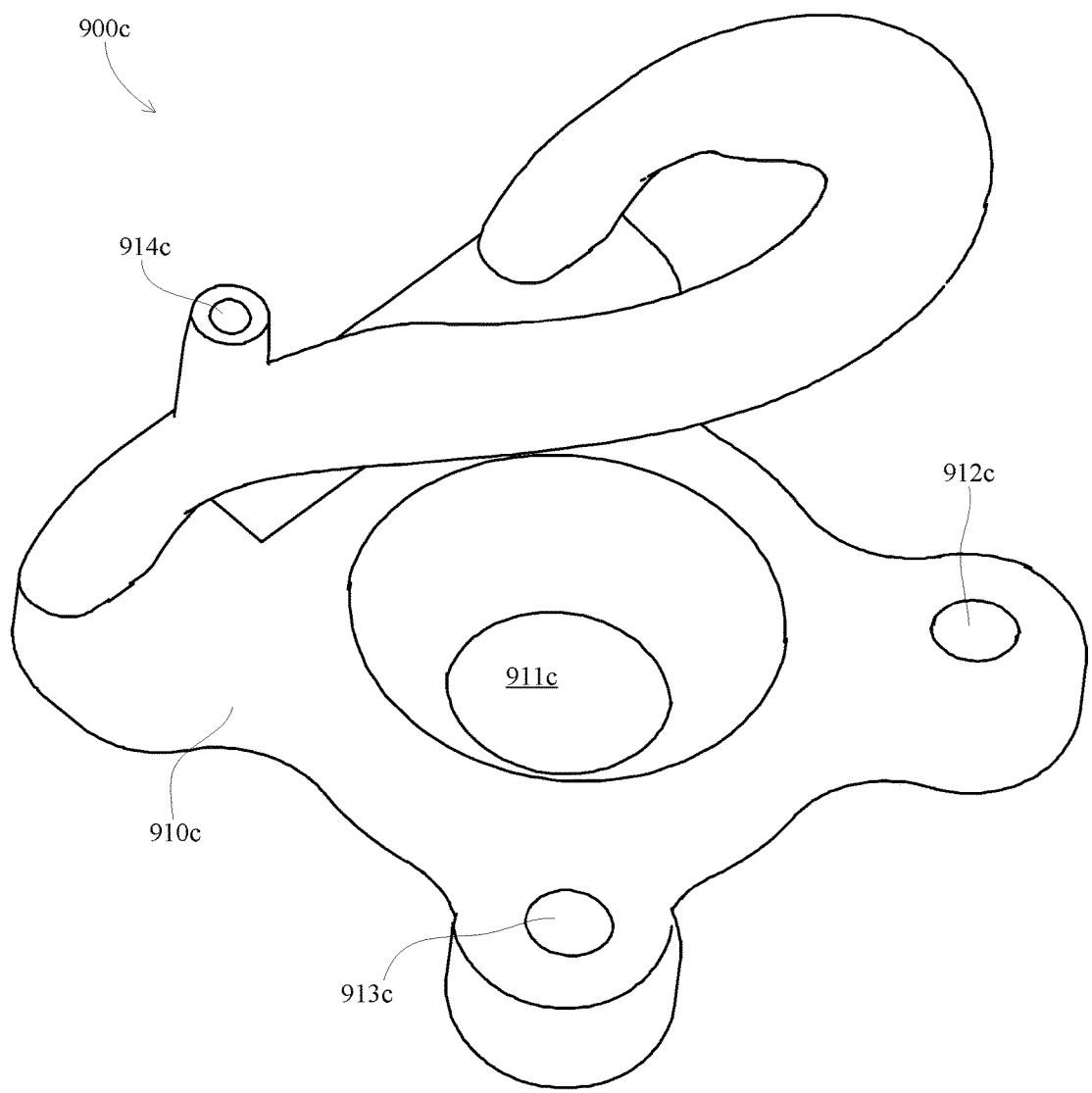
Figure 10A:
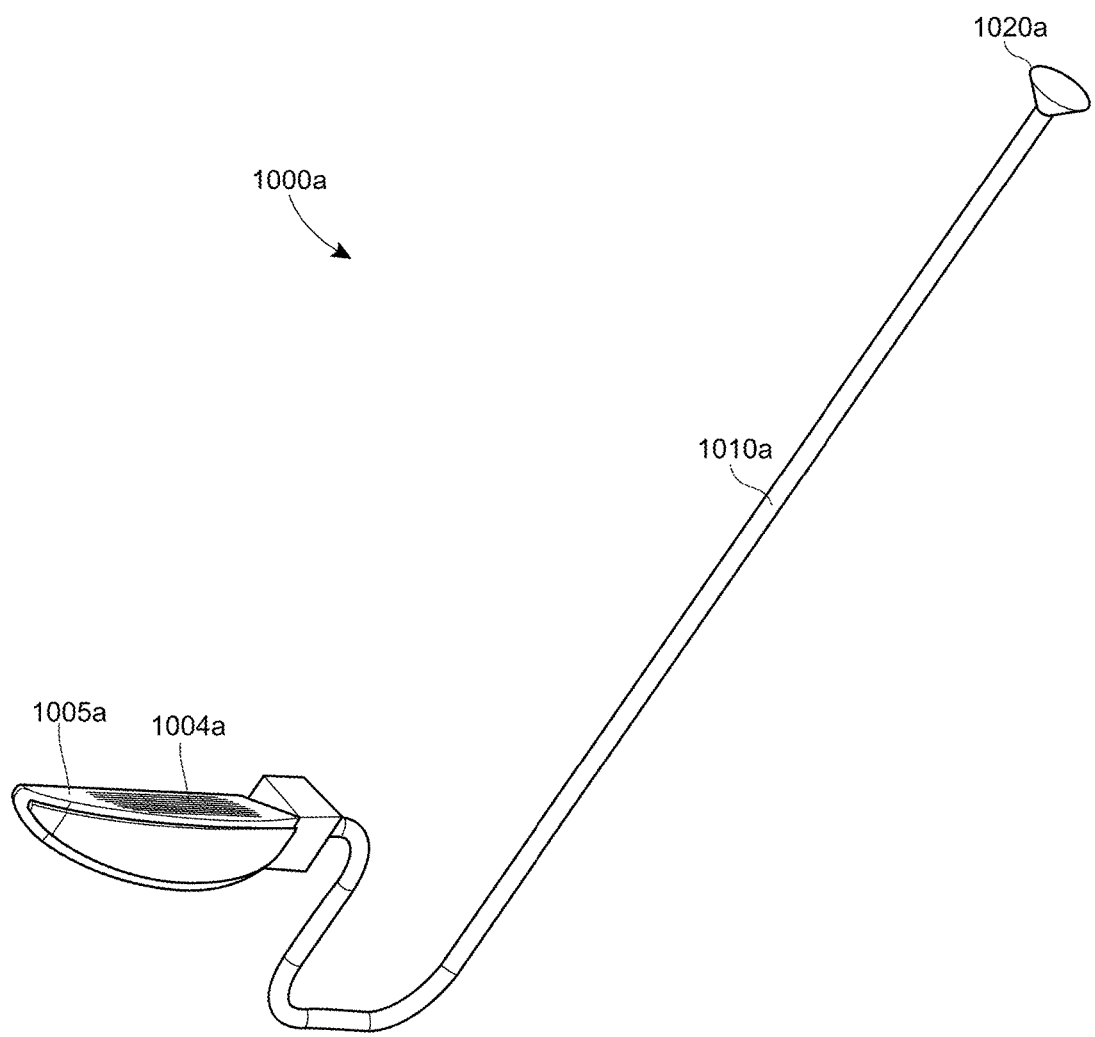
FIGS. 10A-10H, 10J and 10K depict various views of an example illuminated dental wedge assembly.
Figure 10B:
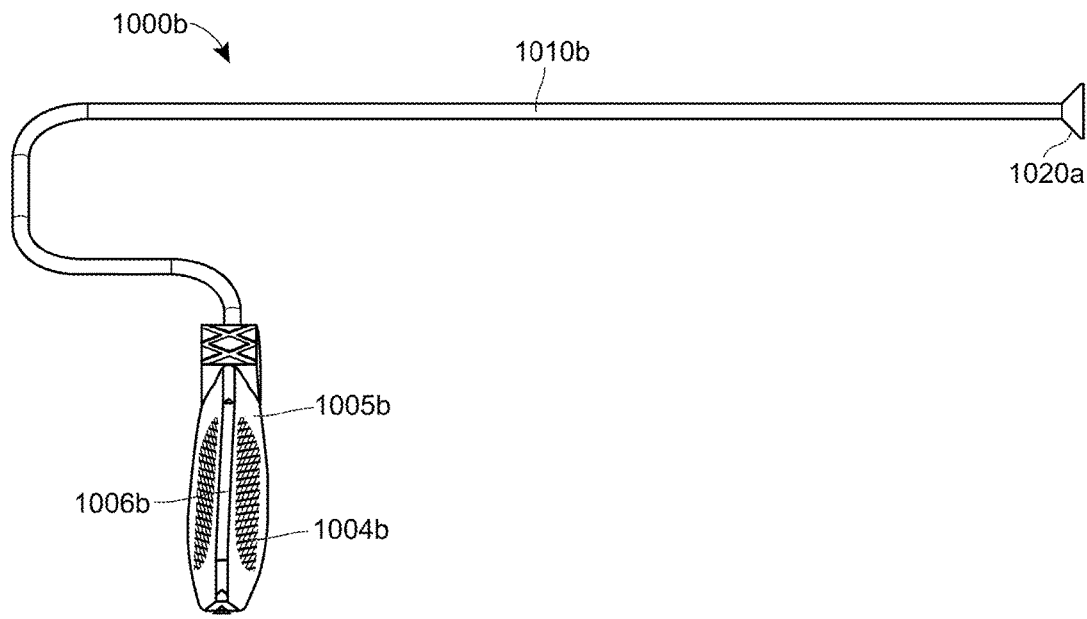
Figure 10C:
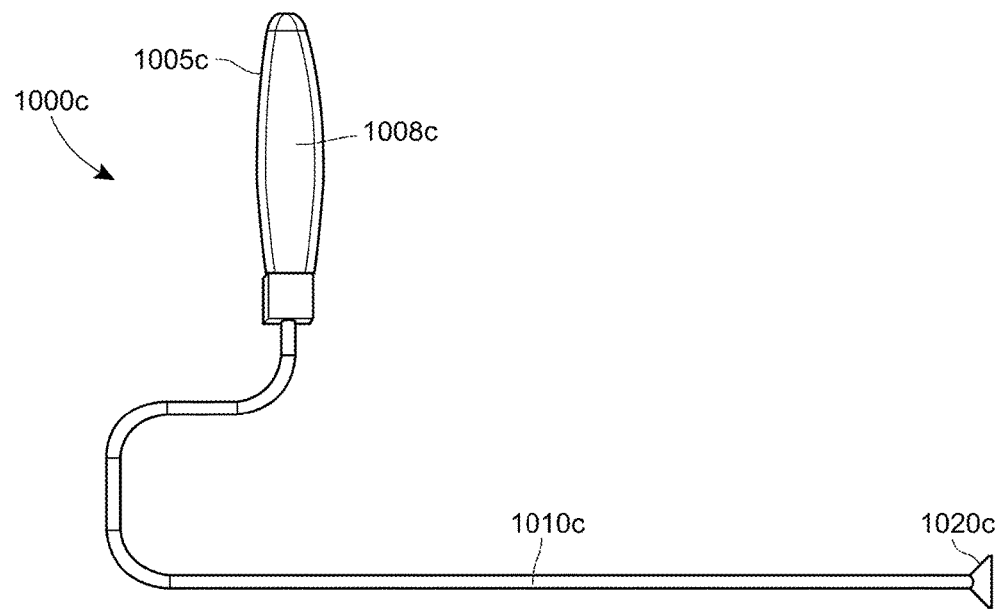
Figure 10D:
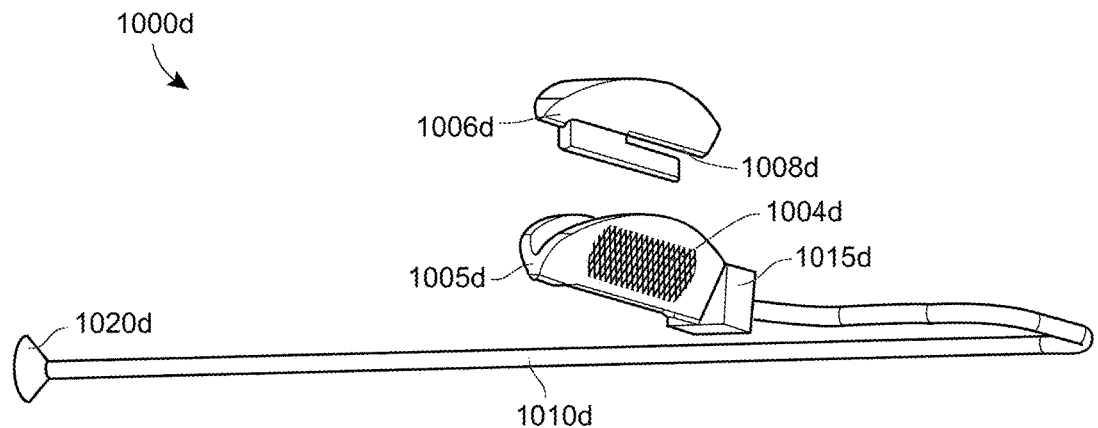
Figure 10E:
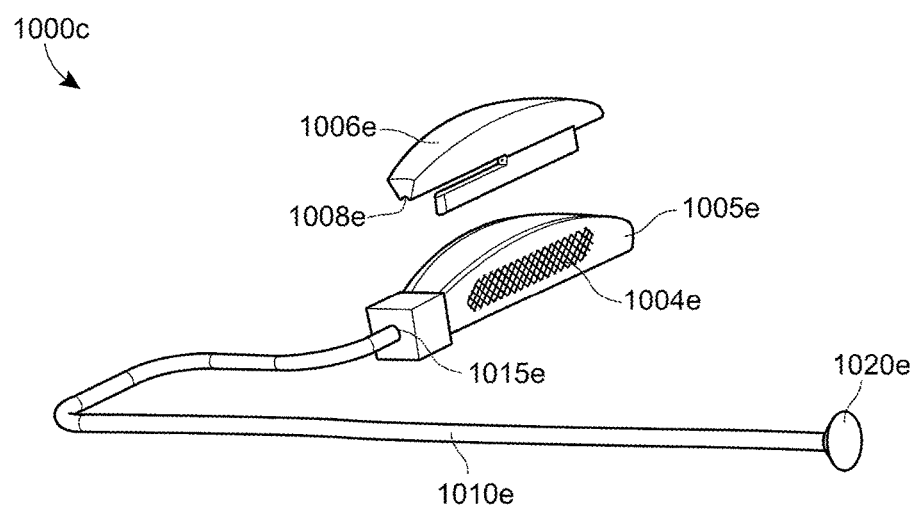
Figure 10F:
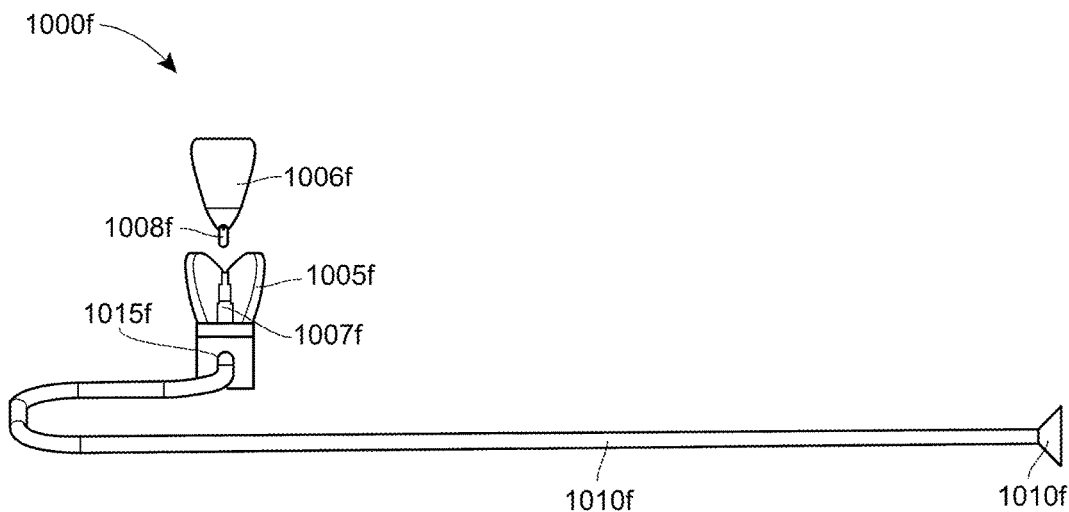
Figure 10G:
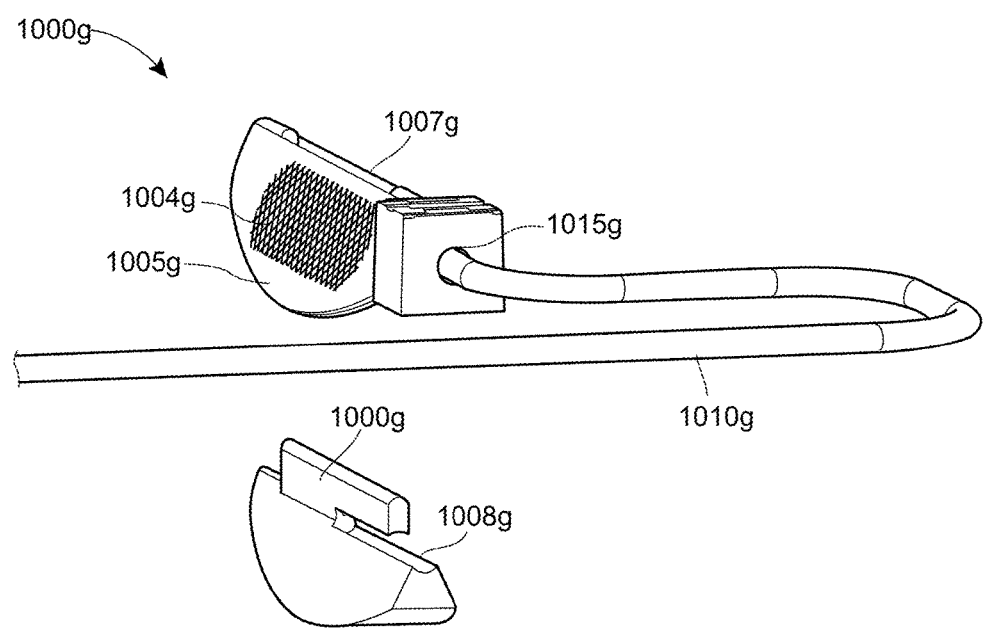
Figure 10H:
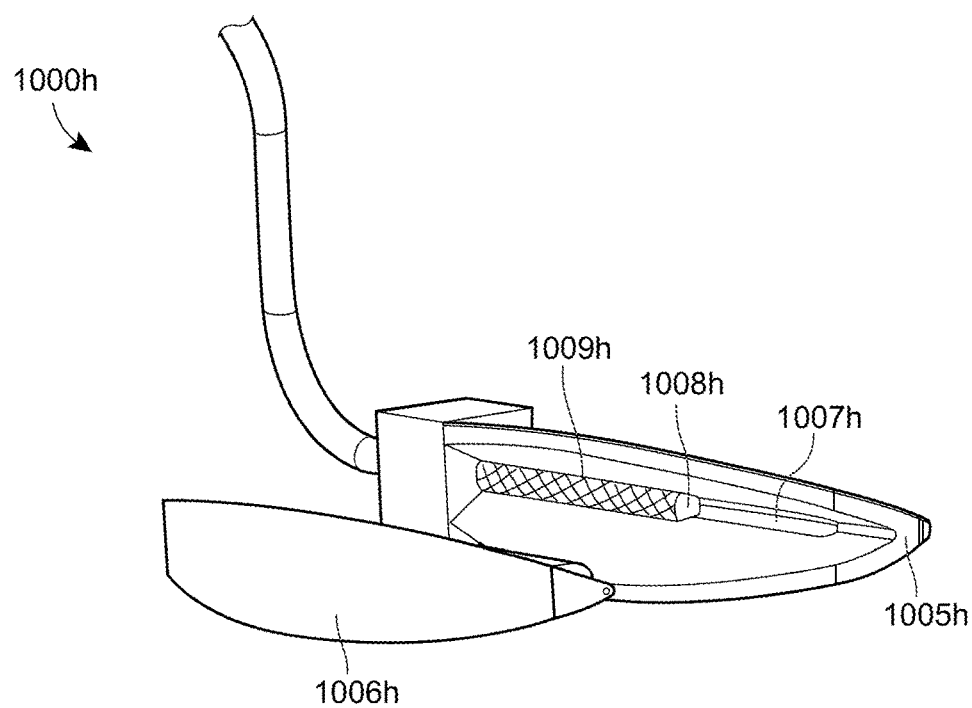
Figure 10J:
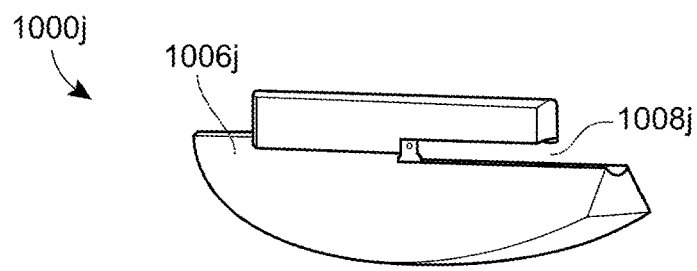
Figure 10K:
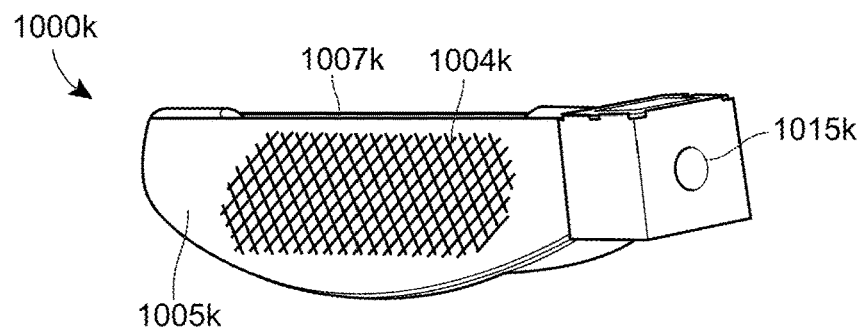

Turning to FIGS. 9A-9C, a cradle assembly 900a-c may include a cradle 910a-c, a light engine 925a,b, and at least one illuminated dental instrument 905b (e.g., an illuminated dental mirror, an illuminated dental wedge, an illuminated dental pick, an illuminated dental bite block, etc.). The light engine 925a,b may include a battery charger receptacle 926b and an on/off pushbutton 926a, 927b.

The cradle 910a-c may include a light engine receptacle 911b, a first illuminated dental instrument receptacle 912a,b, a second illuminated dental instrument receptacle 913b, and a fiber optic cable post 914b,c. The first illuminated dental instrument receptacle 912a,b, the second illuminated dental instrument receptacle 913b, and the fiber optic cable post 914b may include a magnetically energetic material configured to magnetically attract with a magnetic coupler 915b of a respective illuminated dental instrument 905b and/or fiber optic cable magnetic coupler.

With reference to FIGS. 10A-10H, 10J and 10K, an illuminated dental wedge assembly 1000h,j may include a dental wedge shell 1005a, b, d-h,j,k, an optically clear silicone core diffuser 1006b, d-h, a fiber optic light guide 1010a-g, a cone-shaped shoulder 1020a-f, a fiber optic light wave guide channel 1008c-h,j, a light diffuser channel 1007g, a fiber optic light diffuser tip 1009h, a fiber optic light wave guide port 1015d,e,f,g,k, and a textured shell surface 1004a,b,d,e,g,k. The illuminated dental wedge assembly 1000a-h,j,k may be in the field of dental retention devices. The illuminated dental wedge assembly 1000a-h,j,k may illuminate a work area and abutting teeth that the wedge has contact with to assist dentists with visibility while performing class II dental restorations. The shell 1005a,b, c,d-h,j,k may house an optically clear silicone core diffuser 1006b,d-h. A disposable fiber optic light wave guide 1010a-g, with a cone-shaped shoulder on one end 1020a-f, and a diffuser tip on the other 1009h, may be inserted into the fiber optic port 1015d-g,k. The illuminated dental wedge assembly 1000a-h,j,k may allow a dentist to illuminate and inspect a patient's tooth while performing, for example, class II restorations.

Figure 11A:
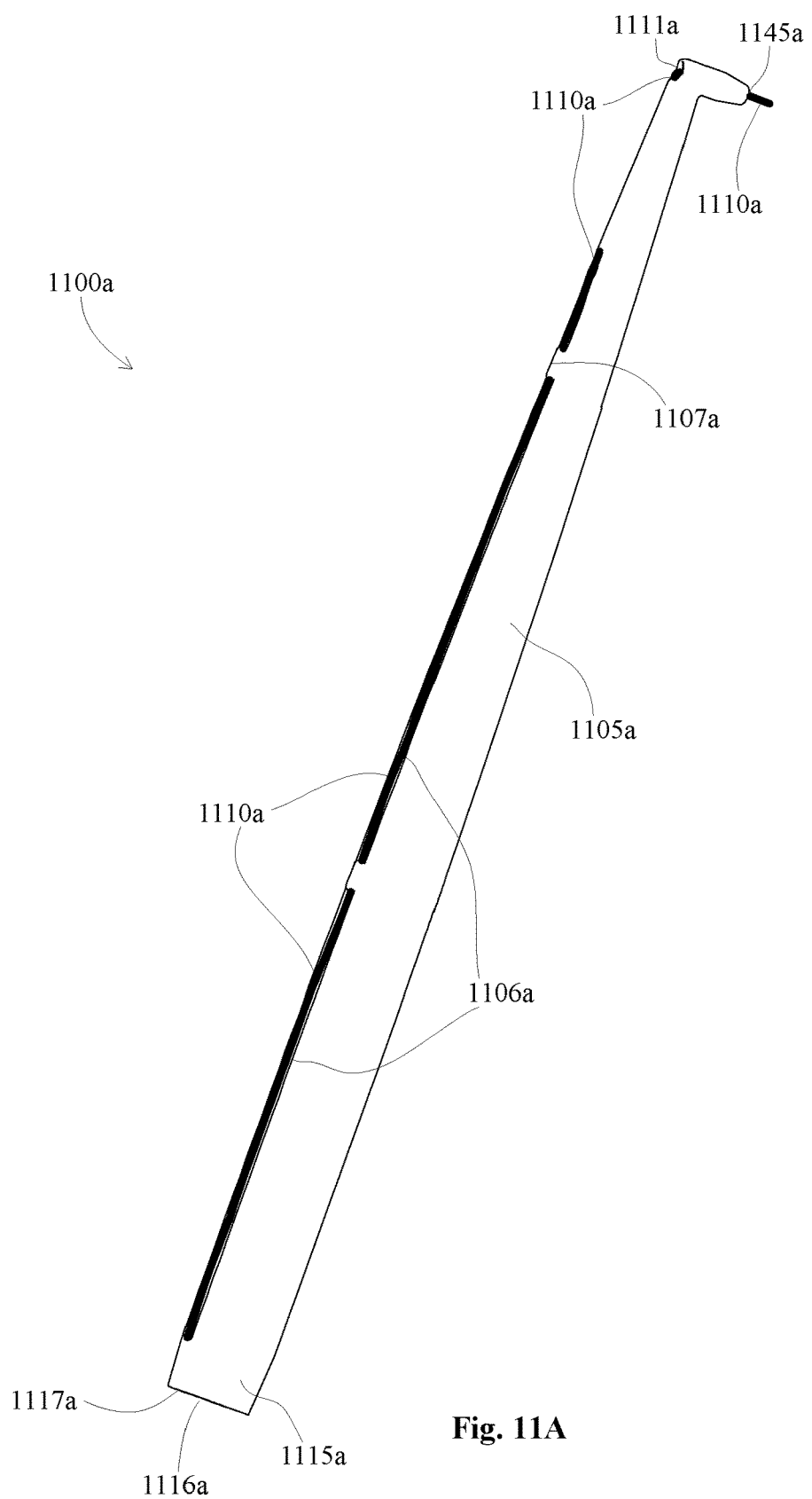
FIGS. 11A-11C depict various views of an example trans-illumination dental instrument assembly.
Figure 11B:
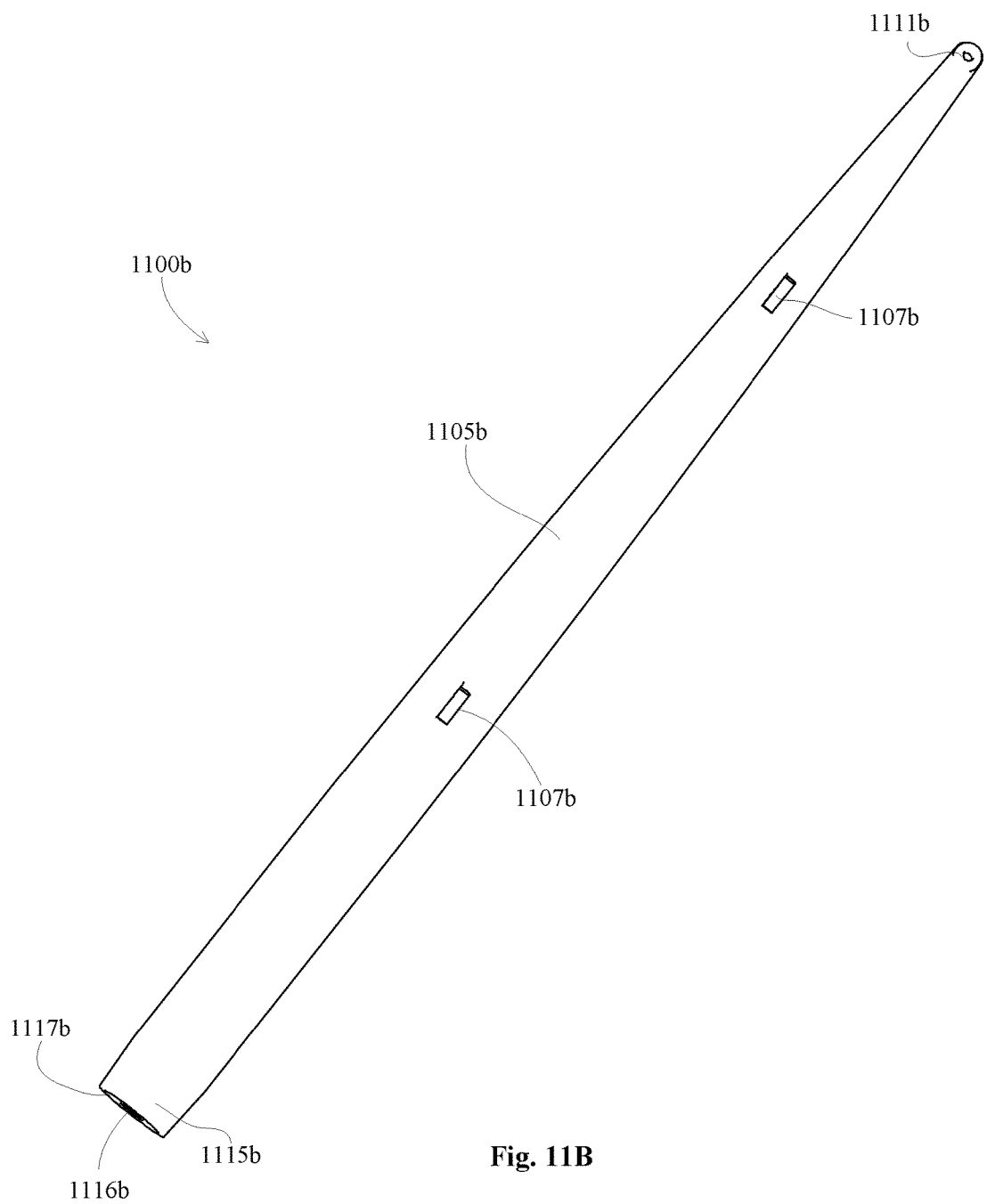
Figure 11C:
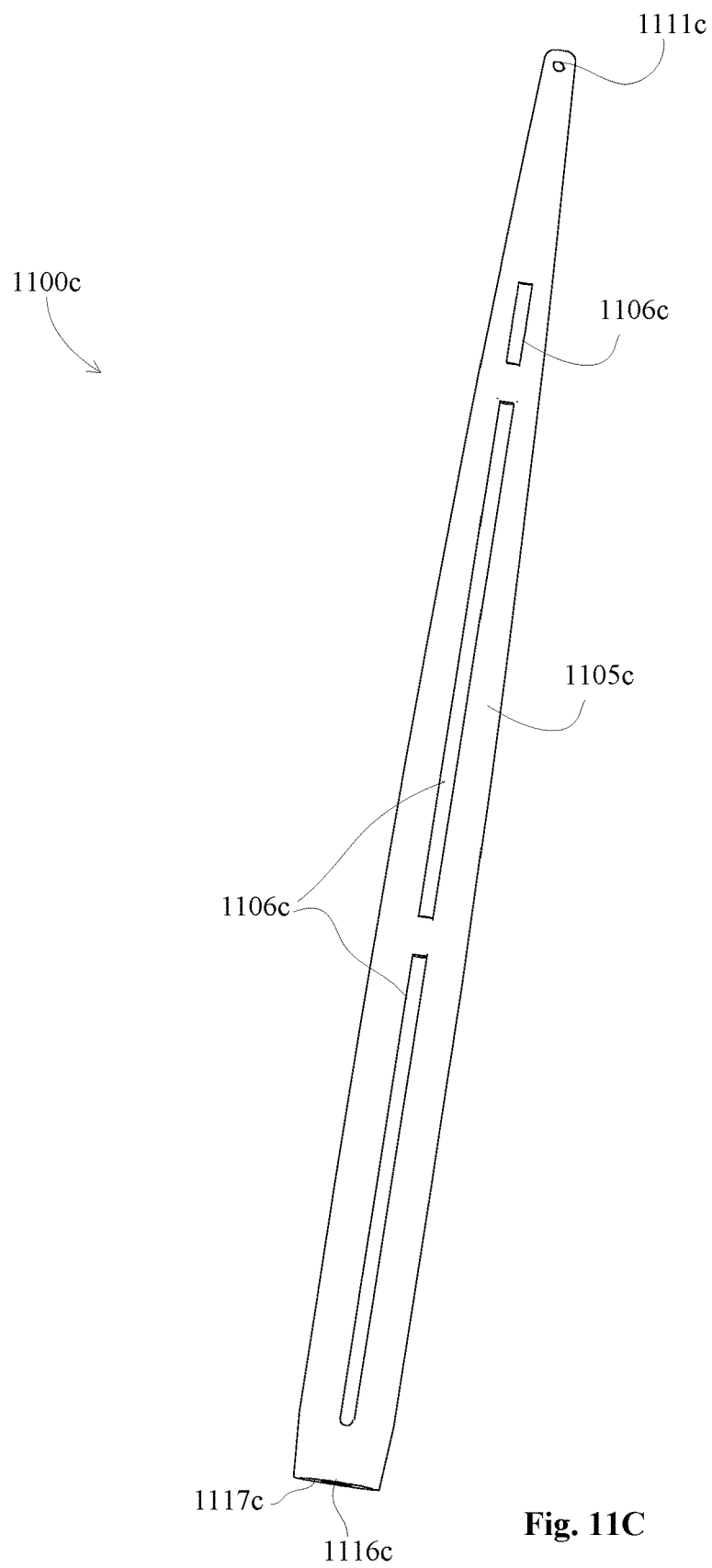

Turning to FIGS. 11A-11C, a trans-illumination dental instrument assembly 1100a-c may include a magnetically coupled fiber optic trans-illumination dental instrument body 1105a-c, a fiber optic light guide 1116a-c, an angled fiber optic light guide tip 1145a, a center passage way for fiber optic cable 1107a,c, a high curie temperature ring magnet pocket 1117a-c, and a high curie temperature ring magnet 1115a,b. The high curie temperature ring magnet 1115a,b may be inserted into an end of the instrument body 1105a,b. The disposable fiber optic wave guide with a funnel shaped end on one side 1116a-c threaded into the center hole in the center of the ring magnet 1115a,b and then may be threaded into the center hole 1107a,c, of the trans-illumination dental instrument body 1105a-c, angled head 1145a.

A user may thread a fiber optic light guide cable 1116a-c through the hole in the high curie temperature magnet 1115a,b, through the body channel 1106a,c/1107a,b, and then through hole 1111a-c in the instrument body's angled head 1145a. The high temperature magnet may be attracted to a female magnetic coupler that may be attached to a light engine 125. When finished, a user may cut the fiber optic light guide 1116a-c, in half and may discard the fiber optic light cable, and then may disinfect (or sterilize) the instrument body 1105a-c in, for example, an autoclave to be used again.

Various size diameter fiber optic light guide cable may be used depending on an amount of light desired. The magnet 1115a,b may be replaced and made with any furious material. The magnetically coupled fiber optic trans-illumination dental instrument head 1145a may have various angles depending on an associated dental procedure to be performed.

The magnetically coupled fiber optic trans-illumination dental instrument 1100a-c for dentistry may also be used for other medical uses outside of dentistry.

Figure 12A:
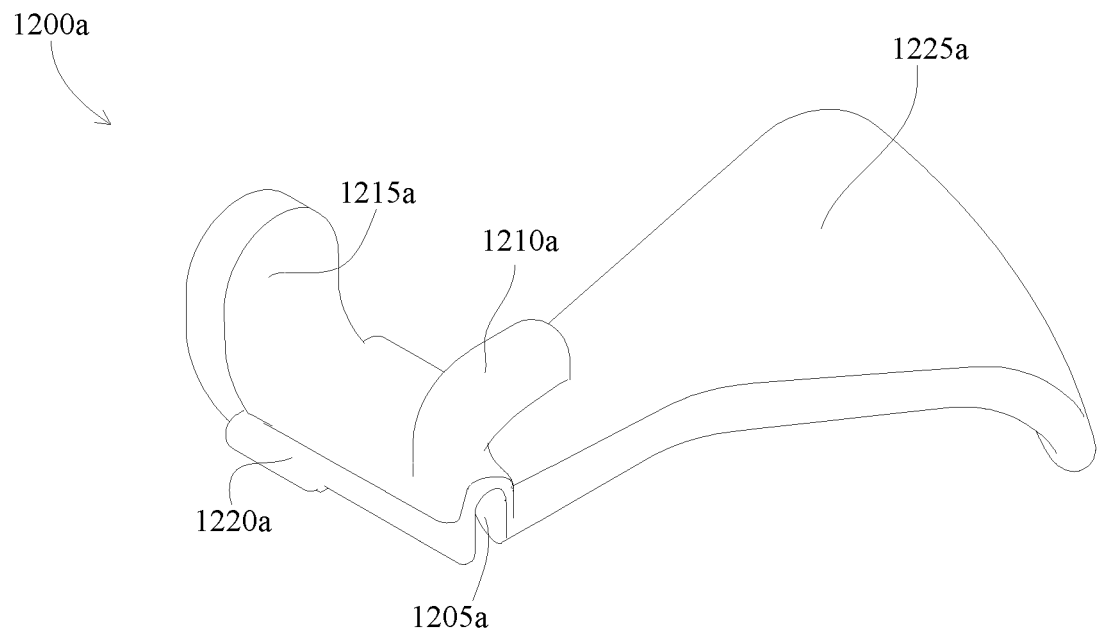
FIG. 12A depicts a top perspective view of an example illuminated tongue depressor assembly.

With reference to FIG. 12A, an illuminated tongue suppressor assembly 1200a may include a fiber optic element opening 1205a, a fiber optic element channel 1210a, a magnetically energetic material 1215a, a mounting base 1220a, and a tongue suppressor 1225a. The fiber optic element opening 1205a and the fiber optic element channel 1210a may be configured to receive a portion of a fiber optic element (e.g., 711b, 718b of FIG. 7B). Alternatively, the fiber optic element opening 1205a and the fiber optic element channel 1210a may be configured to receive a portion of a fiber optic element (e.g., 260b of FIG. 2B) along with an adhesive 285b to secure the fiber optic element within at least a portion of the fiber optic element channel 1210a. The magnetically energetic material 1215a and the mounting base 1220a may be configured to secure the illuminated tongue suppressor assembly 1200a proximate to, for example, a bite block (e.g., bite block 705a of FIG. 7A). The tongue suppressor 1225a may be configured to, for example, suppress a tongue of a dental patient. The illuminated tongue suppressor assembly 1200a may be configured to illuminate an interior portion of a mouth of a dental patient similar to, for example, the illuminated dental mirror assembly 200b of FIG. 2B.

Figure 12B:
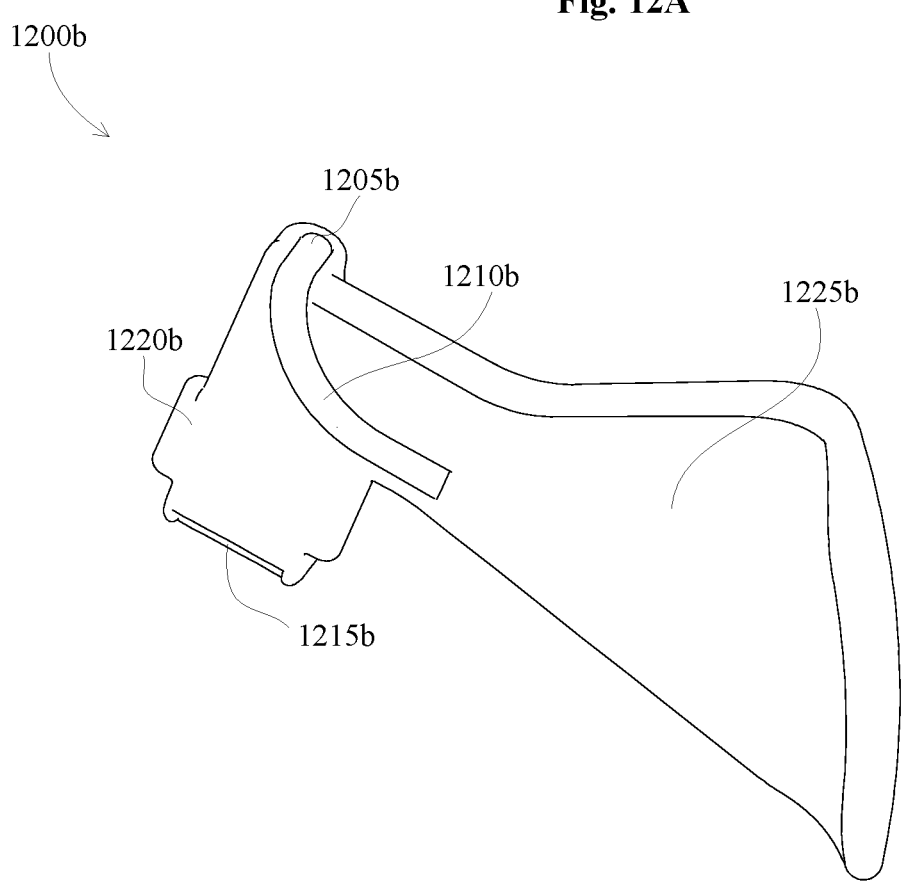
FIG. 12B depicts a bottom perspective view of the example illuminated tongue depressor assembly of FIG. 12A.

Turning to FIG. 12B, an illuminated tongue suppressor assembly 1200b may include a fiber optic element opening 1205b, a fiber optic element channel 1210b, a magnetically energetic material 1215b, a mounting base 1220b, and a tongue suppressor 1225b. The illuminated tongue suppressor assembly 1200b may be similar to, for example, the illuminated tongue suppressor assembly 1200a of FIG. 12A. The fiber optic element opening 1205b and the fiber optic element channel 1210b may be configured to receive a portion of a fiber optic element (e.g., 711b, 718b of FIG. 7B). Alternatively, the fiber optic element opening 1205b and the fiber optic element channel 1210b may be configured to receive a portion of a fiber optic element (e.g., 260b of FIG. 2B) along with an adhesive 285b to secure the fiber optic element within at least a portion of the fiber optic element channel 1210b. The magnetically energetic material 1215b and the mounting base 1220b may be configured to secure the illuminated tongue suppressor assembly 1200b proximate to, for example, a bite block (e.g., bite block 705a of FIG. 7A). The tongue suppressor 1225b may be configured to, for example, suppress a tongue of a dental patient. The illuminated tongue suppressor assembly 1200b may be configured to illuminate an interior portion of a mouth of a dental patient similar to, for example, the illuminated dental mirror assembly 200b of FIG. 2B.

Figure 13A:
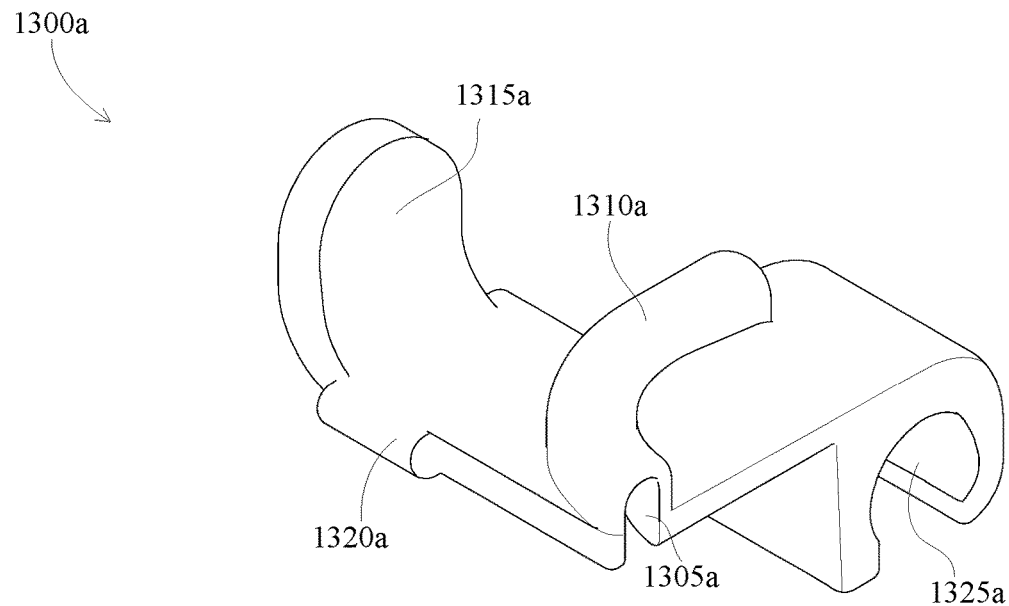
FIG. 13A depicts a top perspective view of an example illuminated saliva ejection tube assembly.

With reference to FIG. 13A, an illuminated saliva ejection tube assembly 1300a (e.g., a high-volume evacuation (HVE) tube holder) may include a fiber optic element opening 1305a, a fiber optic element channel 1310a, a magnetically energetic material 1315a, a mounting base 1320a, and a saliva ejection tube holder 1325a. The fiber optic element opening 1305a and the fiber optic element channel 1310a may be configured to receive a portion of a fiber optic element (e.g., 711b, 718b of FIG. 7B). The magnetically energetic material 1315a and the mounting base 1320a may be configured to secure the illuminated saliva ejection tube assembly 1300a proximate to, for example, a bite block (e.g., bite block 705a of FIG. 7A). Alternatively, the fiber optic element opening 1305a and the fiber optic element channel 1310a may be configured to receive a portion of a fiber optic element (e.g., 260b of FIG. 2B) along with an adhesive 285b to secure the fiber optic element within at least a portion of the fiber optic element channel 1310a. The saliva ejection tube assembly 1325a may be configured to, for example, eject saliva from a mouth of a dental patient. The illuminated saliva ejection tube assembly 1300a may be configured to illuminate an interior portion of a mouth of a dental patient similar to, for example, the illuminated dental mirror assembly 200b of FIG. 2B.

Figure 13B:
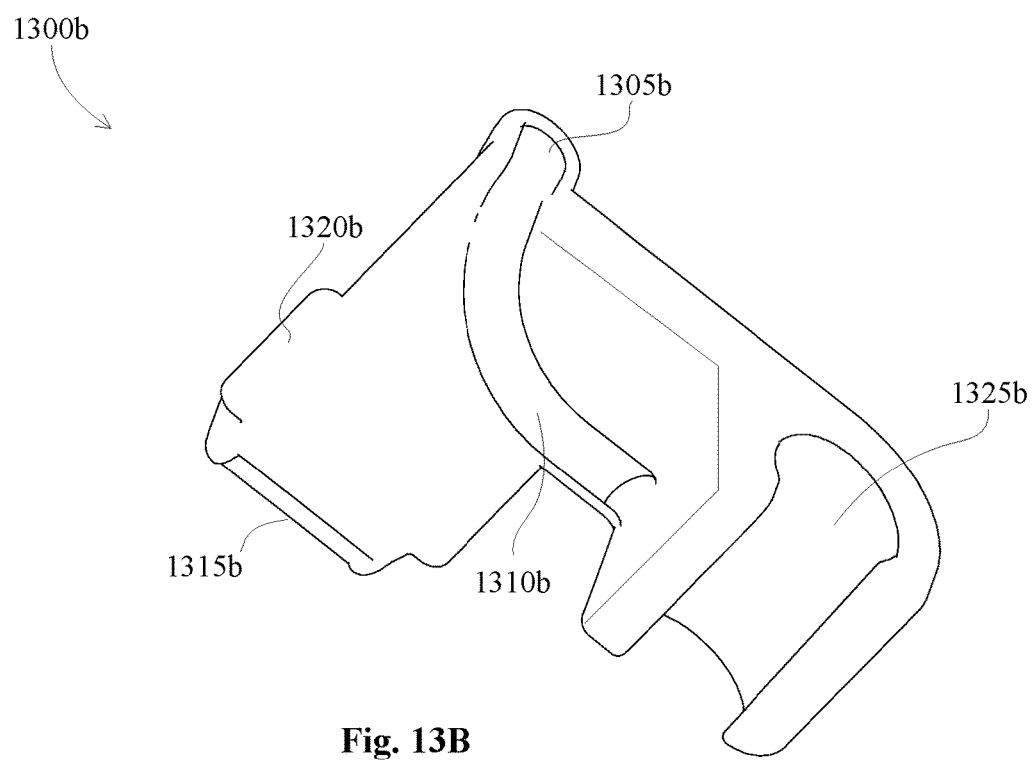
FIG. 13B depicts a bottom perspective view of the example illuminated saliva ejection tube assembly of FIG. 13A.

Turning to FIG. 13B, an illuminated saliva ejection tube assembly 1300b may include a fiber optic element opening 1305b, a fiber optic element channel 1310b, a magnetically energetic material 1315b, a mounting base 1320b, and a saliva ejection tube holder 1325b. The illuminated saliva ejection tube assembly 1300b may be similar to, for example, the illuminated saliva ejection tube assembly 1300a of FIG. 13A. The fiber optic element opening 1305b and the fiber optic element channel 1310b may be configured to receive a portion of a fiber optic element (e.g., 711b, 718b of FIG. 7B). The magnetically energetic material 1315b and the mounting base 1320b may be configured to secure the illuminated saliva ejection tube assembly 1300b proximate to, for example, a bite block (e.g., bite block 705a of FIG. 7A). Alternatively, the fiber optic element opening 1305b and the fiber optic element channel 1310b may be configured to receive a portion of a fiber optic element (e.g., 260b of FIG. 2B) along with an adhesive 285b to secure the fiber optic element within at least a portion of the fiber optic element channel 1310b. The saliva ejection tube assembly 1325b may be configured to, for example, eject saliva from a mouth of a dental patient and/or inject water into the mouth of the dental patient. The illuminated saliva ejection tube assembly 1300b may be configured to illuminate an interior portion of a mouth of a dental patient similar to, for example, the illuminated dental mirror assembly 200b of FIG. 2B.

Figure 14A:
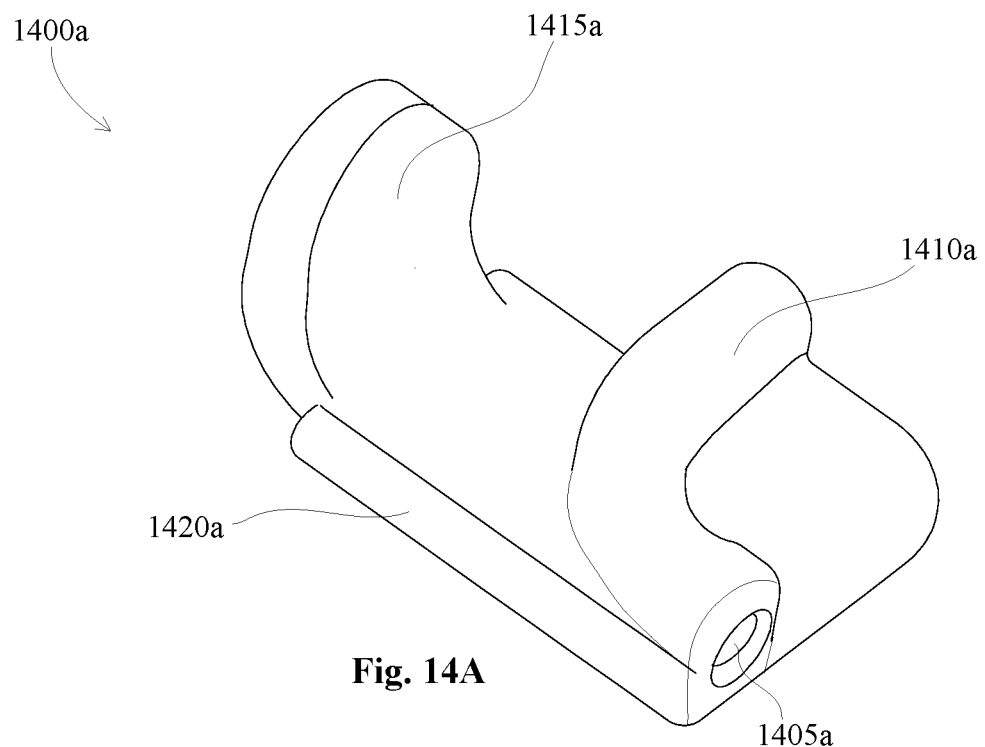
FIG. 14A depicts a top perspective view of an example inter-oral illumination emitter assembly.

With reference to FIG. 14A, an inter-oral illumination emitter assembly 1400a may include a fiber optic element opening 1405a, a fiber optic element channel 1410a, a magnetically energetic material 1415a,b, and a mounting base 1420a. The fiber optic element opening 1405a and the fiber optic element channel 1410a may be configured to receive a portion of a fiber optic element (e.g., 711b, 718b of FIG. 7B). Alternatively, the fiber optic element opening 1405a and the fiber optic element channel 1410a may be configured to receive a portion of a fiber optic element (e.g., 260b of FIG. 2B) along with an adhesive 285b to secure the fiber optic element within at least a portion of the fiber optic element channel 1410a. The magnetically energetic material 1415a and the mounting base 1420a may be configured to secure the inter-oral illumination emitter assembly 1400a proximate to, for example, a bite block (e.g., bite block 705a of FIG. 7A). The inter-oral illumination emitter assembly 1400a may be configured to, for example, illuminate at least a portion of an interior of a mouth of a dental patient. For example, the inter-oral illumination emitter assembly 1400a may be configured to illuminate an interior portion of a mouth of a dental patient similar to, for example, the illuminated dental mirror assembly 200b of FIG. 2B.

Figure 14B:
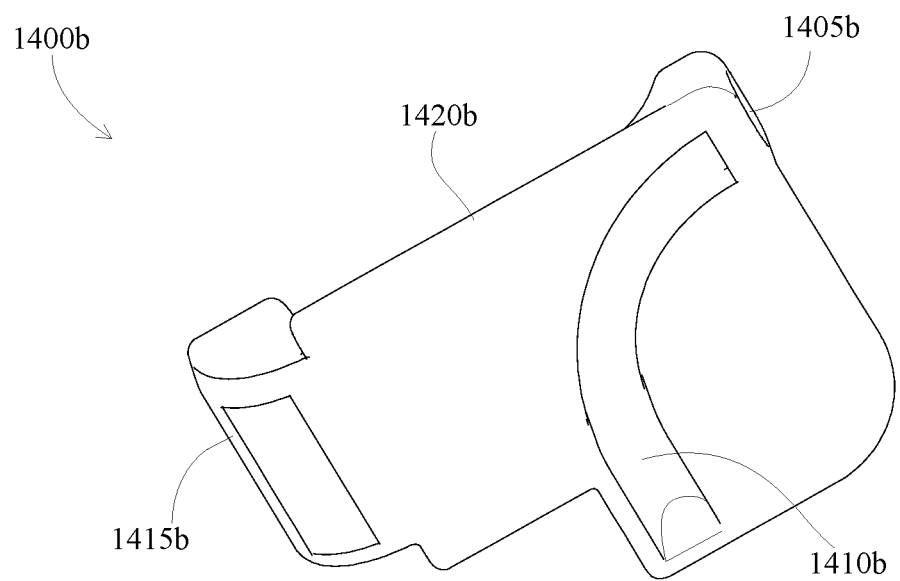
FIG. 14B depicts a bottom perspective view of the example inter-oral illumination emitter assembly of FIG. 14A.

Turning to FIG. 14B, an inter-oral illumination emitter assembly 1400b may include a fiber optic element opening 1405b, a fiber optic element channel 1410b, a magnetically energetic material 1415b, and a mounting base 1420b. The inter-oral illumination emitter assembly 1400b may be similar to, for example, the inter-oral illumination emitter assembly 1400a of FIG. 14A. The fiber optic element opening 1405b and the fiber optic element channel 1410b may be configured to receive a portion of a fiber optic element (e.g., 711b, 718b of FIG. 7B). Alternatively, the fiber optic element opening 1405b and the fiber optic element channel 1410b may be configured to receive a portion of a fiber optic element (e.g., 260b of FIG. 2B) along with an adhesive 285b to secure the fiber optic element within at least a portion of the fiber optic element channel 1410b. The magnetically energetic material 1415b and the mounting base 1420b may be configured to secure the inter-oral illumination emitter assembly 1400b proximate to, for example, a bite block (e.g., bite block 705a of FIG. 7A). The inter-oral illumination emitter assembly 1400b may be configured to, for example, illuminate at least a portion of an interior of a mouth of a dental patient. For example, the inter-oral illumination emitter assembly 1400b may be configured to illuminate an interior portion of a mouth of a dental patient similar to, for example, the illuminated dental mirror assembly 200b of FIG. 2B.

A neodymium magnet may be formed from an axially magnetized sintered neodymium. A surface layer of the neodymium permanent magnet may be encapsulated.

An illuminated dental instrument assembly may be fabricated from a clear plastic material that, when exposed to a source of intense light, effectively becomes an illumination device within the patient's mouth. One such material appropriate for use in this illuminated application is polymethyl methacrylate (PMMA), which provides very good light transmission throughout the structure of any article manufactured therefrom. An illuminated dental mirror assembly may include at least one thin layer of a liquid optically clear (LOC) adhesive (not shown) that is cured by UV radiation.

A light engine may be a Model No. HYLUX-STM-B as available from Ascentcare Dental Labs, Inc., Nunica, Mich. This light engine 200 features a Cree XP-L HI LED light source 202 with a maximum output of 1100 lumens or 160,000 cd candela. This light engine offers three brightness levels: 1100 lumens, 550 lumens, and 80 lumens. An associated fiber optic cable may be adapted for use in an autoclave machine for sterilization of the fiber optic cable. A benefit of the use of polycarbonate materials in conjunction with the light engine is that polycarbonate plastic filters ultraviolet or UV or blue light radiation. The dental profession has recently moved toward use of polymerization of blue light cure resin based composites and blue light curable resins to adhere dental appliances to a patient's mouth and/or teeth. Thus, it may be desirable that light being provided to a dental patient's mouth not contain UV radiation, and that the dentist and and/or dental hygienist be provided with the highest level of control over the application of blue light to a dental patient.

It will be understood by one having ordinary skill in the art that construction of the described invention and other components is not limited to any specific material. Other exemplary embodiments of the invention disclosed herein may be formed from a wide variety of materials, unless described otherwise herein.

The fiber optic cable 110 and/or fiber optic element 260b, c may include at least one optical fiber having a transparent core surrounded by a transparent cladding material with a lower index of refraction than the optical fiber. Photons may propagate along the optical fiber due to total internal reflection at an intersection of the optical fiber and the transparent cladding material, which may cause the optical fiber to function as a waveguide. The fiber optic cable 110 and/or fiber optic element 260b, c may include optical fibers having a plurality of propagation paths or transverse modes (i.e., multi-mode fibers (MMF)) or a single mode (i.e., single-mode fibers (SMF)). Photon transmission through the optical fibers may be unaffected by other electromagnetic radiation nearby. The optical fiber may be electrically nonconductive, such that the fiber optic cable 110 and/or fiber optic element 260b, c does not act as an antenna or couple with electromagnetic signals. Photons traveling inside the optical fiber may be immune to electromagnetic interference, even electromagnetic pulses generated by nuclear devices (e.g., Xray machines, etc.). An optical fiber may be a cylindrical dielectric waveguide (nonconducting waveguide) that may transmit photons along a longitudinally extending axis via, for example, total internal reflection. An optical fiber may consist of a core surrounded by a cladding layer. Both the core and the cladding of the optical fiber may be manufactured of dielectric materials. To confine the optical signal in the core, the refractive index of the core may be greater than that of the cladding. A boundary between the core and cladding may either be abrupt, in step-index fiber, or gradual, in graded-index fiber. Rough and/or irregular surfaces, even at a molecular level, may cause photons to be reflected in random directions (i.e., this is often referred to as diffuse reflection or scattering, and it is typically characterized by wide variety of reflection angles). Accordingly, rough and/or irregular surfaces within the fiber optic cable 110 and/or fiber optic element 260b, c and/or at ends of the fiber optic cable 110 and/or fiber optic element 260b, c may be minimized. Photon scattering within the fiber optic cable 110 and/or fiber optic element 260b, c and/or at ends of the fiber optic cable 110 and/or fiber optic element 260b, c may depend on a wavelength of the light being transmitted within the fiber optic cable 110 and/or fiber optic element 260b, c. Thus, limits to spatial scales of visibility may arise, depending on a frequency of the incident light-wave and the physical dimension (or spatial scale) of a scattering center, which is typically in the form of some specific micro-structural feature. Since visible light may have a wavelength of an order of one micrometer (one millionth of a meter) scattering centers may have dimensions on a similar spatial scale. Thus, attenuation may result from an incoherent scattering of light at internal surfaces of the fiber optic cable 110 and/or fiber optic element 260b, c and interfaces at the ends of the fiber optic cable 110 and/or fiber optic element 260b, c. In (poly)crystalline materials such as metals and ceramics, in addition to pores, most of the internal surfaces or interfaces may be in a form of grain boundaries that may separate tiny regions of crystalline order. It has recently been shown that when a size of a scattering center (or grain boundary) is reduced below the size of the wavelength of the light being scattered, the scattering no longer occurs to any significant extent. This phenomenon has given rise to the production of transparent ceramic materials. The fiber optic cable 110 and/or fiber optic element 260b, c may include scattering center (or grain boundary) that is below a size of a wavelength of light being transmitted via the fiber optic cable 110 and/or fiber optic element 260b, c. The fiber optic cable 110 and/or fiber optic element 260b, c may include a transparent ceramic material.

Similarly, scattering of light in an optical quality glass fiber may be caused by molecular level irregularities (compositional fluctuations) in an associated glass structure. Indeed, a glass may be a limiting case of a polycrystalline solid. Within this framework, "domains" exhibiting various degrees of short-range order become the building blocks of both metals and alloys, as well as glasses and ceramics. Distributed both between and within these domains are micro-structural defects that provide locations for light scattering. This same phenomenon is seen as one of the limiting factors in the transparency of IR missile domes.

At high optical powers, scattering can also be caused by nonlinear optical processes in the optical fiber. In addition to light scattering, attenuation or signal loss can also occur due to selective absorption of specific wavelengths of light, in a manner similar to that responsible for the appearance of color. Primary material considerations include both electrons and molecules. At an electronic level, fiber optic cable 110 and/or fiber optic element 260b, c material may depend on whether electron orbitals are spaced (or "quantized") such that the electrons can absorb a quantum of light (or photon) of a specific wavelength or frequency in the ultraviolet (UV) or visible ranges. This may give rise to color. At an atomic or molecular level, fiber optic cable 110 and/or fiber optic element 260b, c material considerations may depend on frequencies of atomic or molecular vibrations or chemical bonds, how close-packed atoms or molecules are, and whether or not the atoms or molecules exhibit long-range order. These factors may determine the capacity of the fiber optic cable 110 and/or fiber optic element 260b, c material transmitting longer wavelengths in an infrared (IR), far IR, radio and microwave ranges.

Design of an optically transparent device (e.g., fiber optic cable 110, fiber optic element 260b, c, etc.) may include selection of materials based upon knowledge of the optically transparent device properties and limitations. Lattice absorption characteristics observed at lower frequency regions (i.e., mid IR to far-infrared wavelength range) define the long-wavelength transparency limit of the material. The lattice absorption characteristics may result from an interactive coupling between motions of thermally induced vibrations of constituent atoms and molecules of a solid lattice and incident light wave radiation. Hence, fiber optic cable 110 and/or fiber optic element 260b, c materials may be bounded by limiting regions of absorption caused by atomic and molecular vibrations (bond-stretching) in the far-infrared (>10 μm). Multi-phonon absorption may occur within the fiber optic cable 110 and/or fiber optic element 260b, c when two or more phonons simultaneously interact to produce electric dipole moments with which incident radiation may couple. These dipoles may absorb energy from incident radiation, reaching a maximum coupling with radiation when the frequency is equal to the fundamental vibrational mode of the molecular dipole (e.g., Si—O bond) in the far-infrared, or one of its harmonics. The fiber optic cable 110 and/or fiber optic element 260b, c may include a fundamental vibration mode of a molecular dipole that is less than or greater than a frequency of light being transmitted via the fiber optic cable 110 and/or fiber optic element 260b, c. The selective absorption of infrared (IR) light by a particular fiber optic material may occur because a selected frequency of light wave matches a frequency (or an integer multiple of the frequency) at which the particles of that material vibrate. Since different atoms and molecules have different natural frequencies of vibration, they will selectively absorb different frequencies (or portions of the spectrum) of infrared (IR) light.

Reflection and transmission of light waves may occur because frequencies of the light waves do not match a natural resonant frequencies of vibration of the objects. When IR light of these frequencies strikes an object, the energy is either reflected or transmitted. It is often desirable to align an optical fiber with another optical fiber, or with an optoelectronic device such as a light-emitting diode, a laser diode, or a modulator. This can involve either carefully aligning the optical fibers and placing the optical fiber in contact with the device. Alternatively, a lens may be used to facilitate coupling over an air gap. In some cases an end of the optical fiber may be polished into a curved form that makes it act as a lens. An end of an optical fiber may be formed into a lens by cutting the optical fiber with a laser. A bare fiber ends may be coupled using a fiber launch system, which may use a microscope objective lens to focus photons down to a fine point. A precision translation stage (e.g., a micro-positioning table) may be used to move the lens, fiber, or device to allow coupling efficiency to be optimized. Optical fibers with a coupler on an end make the coupling process (i.e., a coupler may be plugged into a pre-aligned fiber optic collimator, which may contain a lens that is either accurately positioned with respect to the fiber, or is adjustable). Photon injection efficiency may be achieved into a single-mode fiber by controlling a direction, position, size and/or a divergence of a photon beam. The fiber optic cable 110 and/or fiber optic element 260b, c may achieve 70 to 90% coupling efficiency. With properly polished single-mode fibers, an emitted photon beam may have a Gaussian shape, even in a far field. An associated lens may be large enough to support full numerical aperture of the optical fiber, such that the lens does not introduce aberrations in an associated photon beam. An aspheric lens may be used.

A refractive index of optical fibers may vary slightly based on a frequency of light. Light source 125 may not be monochromatic. Modulation of the light source 125, to transmit a signal, may also slightly widen a frequency band of transmitted light. This may have an effect that, over long distances and at high modulation speeds, different frequencies of light may take different times to arrive at an illuminated dental mirror assembly 105. An optical fiber may include an opposite refractive index gradient.

The first and second magnetic light couplers 115, 120 may include an axially magnetized planar single-mode fiber optic linear magnetic coupling system. The first and second magnetic light couplers 115, 120 may be configured such that associated magnetic flux may be transferred about a flat end of ring faces of an associated magnetically energetic material 270b, c, allowing quick and easy one handed assembly and disassembly while allowing quick and easy changing of accessory dental instruments (e.g., an illuminated dental mirror assembly 105). The first and second magnetic light couplers 115, 120 may be attracted to one and other, and may include additional thrust bearing support. Light entering an input fiber may appear at one or more outputs and light power distribution may depend on an associated wavelength and polarization. The first and second magnetic light couplers 115, 120 may be fabricated in different ways, for example by thermally fusing fibers so that the fiber optic cable 110 and/or fiber optic element 260b, c are communicatively coupled. The first and second magnetic light couplers 115, 120 may combine two inputs at different wavelengths into one output without exhibiting significant losses.

The first and second magnetic light couplers 115, 120 may be configured such that one member of the coupling is fully nested within an inside diameter of the second member. The two components may share a common axis about which both may rotationally translate. Inherently, linear couplings may align axially. As such, any misalignment may lead to a driver pulling a follower into a desired position. An amount of radial tolerance may be based on a spacing between the driver and the follower. The larger the spacing, the greater tolerance to radial misalignment. An amount of angular tolerance may be based on a spacing between the driver and follower. The larger the free space coupling 115, 120 the spacing, the greater the tolerance to angular misalignment.

The first and second magnetic light couplers 115, 120 may be configured such that a magnetic flux is transferred about the flat end faces of the magnetic assembly. The two components of the first and second magnetic light couplers 115, 120 may be attracted to one and other. Two axially magnetized ring magnets may be embedded into separate tubes with single-mode optical fiber running through a center to connect and disconnect accessory medical instruments (e.g., an illuminated dental mirror assembly 150) to an incoherent light source 125. An objective of an axially magnetized linear type single-mode fiber optic magnetic coupling system (e.g., first and second magnetic light couplers 115, 120) may be to enable changing of accessory medical instruments (e.g., an illuminated dental mirror assembly 105) using one hand, and may allow easy quick sterilization of accessory medical devices. Another objective of the optical fiber coupling system (e.g., first and second magnetic light couplers 115, 120) may allow for the use of cost effective disposable fiber optic light guides (e.g., fiber optic cable 110, fiber optic element 260b,c, fiber optic element 1010a-g, etc.). A linear coupling design (e.g., first and second magnetic light couplers 115, 120 design) may be a planar type configured such that an associated magnetic flux may be transferred about flat end faces of an associated magnetic ring assembly. The first and second magnetic light couplers 115, 120 may be attracted to one another and may not require additional support for proper alignment, or to enable 360° rotation about when proximate one another.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of this disclosure, the term "operably connected" generally means that one component functions with respect to another component, even if there are other components located between the first and second component, and the term "operable" defines a functional relationship between components.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that, unless otherwise described, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or coupler or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating positions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

What is claimed is:

1. An illuminated dental instrument assembly, comprising:
   a fiber optic cable coupler including a first magnetically energetic material within a first coupler half, wherein the fiber optic cable coupler is configured to allow the illuminated dental instrument assembly to rotate with respect to a second magnetically energetic material within a second coupler half that is attached to an associated fiber optic cable; and
   a handle having a proximal end and a distal end, wherein the fiber optic cable coupler is fixed to the proximal end, that at least partially encapsulates a fiber optic element within a handle material that does not degrade when sterilized in an autoclave, wherein the fiber optic cable coupler is further configured to allow the fiber optic element to rotate with respect to the fiber optic cable.

2. The illuminated dental instrument assembly of claim 1, further comprising:
   a mirror element, fixed to the distal end of the handle, having a reflective surface.

3. The illuminated dental instrument assembly of claim 2, wherein the reflective surface is oriented at an angle between 30° and 60° with respect to a central axis of the handle, and wherein the fiber optic element is configured to transmit up to at least one of: 1100 lumens, 550 lumens, 80 lumens, or 80,000 LUX.

4. The illuminated dental instrument assembly of claim 1, wherein at least one of: the first magnetically energetic material or the second magnetically energetic material is a permanent magnet, wherein magnetic properties of the magnetically energetic material do not degrade at temperatures up to 180° F.

5. The illuminated dental instrument assembly of claim 1, wherein at least one of: the first magnetically energetic material or the second magnetically energetic material is ferromagnetic, wherein magnetic properties of the magnetically energetic material do not degrade at temperatures up to 180° F.

6. The illuminated dental instrument assembly of claim 2, wherein the reflective surface includes at least one of: silver, silver with an indium-tin oxide overcoat, chromium, aluminum, silver-gold alloy, zirconium, or zirconium alloy.

7. The illuminated dental instrument assembly of claim 4, wherein the permanent magnet is comprised of a neodymium high curie temperature magnetic material.

8. An illuminated dental instrument assembly, comprising:
   a fiber optic cable coupler, wherein the fiber optic cable coupler is configured to allow the illuminated dental instrument assembly to rotate with respect to an associated fiber optic cable; and
   a handle having a proximal end and a distal end, wherein the fiber optic cable coupler is fixed to the proximal end, that at least partially encapsulates a fiber optic element within a handle material that does not degrade when sterilized in an autoclave, wherein the fiber optic cable coupler is further configured to allow the fiber optic element to rotate with respect to the fiber optic cable.

9. The illuminated dental instrument assembly of claim 8, wherein the fiber optic coupler includes a magnetically energetic material.

10. The illuminated dental instrument assembly of claim 9, wherein the magnetically energetic material is at least partially enclosed within an end cap/coupling lens.

11. The illuminated dental instrument assembly of claim 8, further comprising:
    a mirror element, fixed to the distal end of the handle, having a reflective surface, wherein the reflective surface includes at least one of: silver, silver with an indium-tin oxide overcoat, chromium, aluminum, silver-gold alloy, zirconium, or zirconium alloy.

12. The illuminated dental instrument assembly of claim 11, wherein the reflective surface is oriented at an angle between 40° and 60° with respect to a central axis of the handle.

13. The illuminated dental instrument assembly of claim 8, wherein at least a portion of the fiber optic element is supported by a core element, wherein the fiber optic element is configured to transmit up to at least one of: 1100 lumens, 550 lumens, 80 lumens, or 80,000 LUX, and wherein at least a portion of the core element is encapsulated within the handle material.

14. The illuminated dental instrument assembly of claim 9, wherein a portion of the fiber element extends through an aperture in the magnetically energetic material.

15. An illuminated dental instrument assembly, comprising:
   a fiber optic cable coupler including a first magnetically energetic material within a first coupler half, wherein the fiber optic cable coupler is configured to allow the illuminated dental instrument assembly to rotate with respect to a second magnetically energetic material within a second coupler half that is attached to an associated fiber optic cable; and
   a handle having a proximal end and a distal end, having a fiber optic element extending from the proximal end of the handle to the distal end of the handle, wherein the fiber optic cable coupler is fixed to the proximal end, and wherein the fiber optic cable coupler is further configured to allow the fiber optic element to rotate with respect to the fiber optic cable.

16. The illuminated dental instrument assembly of claim 15, wherein at least a portion of the fiber optic element is supported by a core element, and wherein at least a portion of the core element and at least a portion of the fiber optic element are encapsulated within a handle material.

17. The illuminated dental instrument assembly of claim 15, further comprising:
   a mirror element, fixed to the distal end of the handle, having a reflective surface, wherein the reflective surface is oriented at an angle between 55° and 60° with respect to a central axis of the handle.

18. The illuminated dental instrument assembly of claim 15, wherein a portion of the fiber element extends through an aperture in the first magnetically energetic material.

19. The illuminated dental instrument assembly of claim 15, wherein at least one of: the first magnetically energetic material or the second magnetically energetic material is at least partially enclosed within an end cap/coupling lens, wherein the end cap/coupling lens includes a light transmitting surface.

20. The illuminated dental instrument assembly of claim 15, wherein at least one of: the first magnetically energetic material or the second magnetically energetic material is selected from a group of materials including: a magnetic material, a ferrous metal, a ferrous metal alloy, ferromagnetic material, a permanent magnet, or a neodymium (NdFeB) high curie temperature ($T_c$) magnetic material, wherein magnetic properties of the magnetically energetic material do not degrade at temperatures up to 180° F.

* * * * *